United States Patent [19]
Venkataraman et al.

[11] Patent Number: 5,619,421
[45] Date of Patent: Apr. 8, 1997

[54] COMPUTER-IMPLEMENTED PROCESS AND COMPUTER SYSTEM FOR ESTIMATING THE THREE-DIMENSIONAL SHAPE OF A RING-SHAPED MOLECULE AND OF A PORTION OF A MOLECULE CONTAINING A RING-SHAPED STRUCTURE

[75] Inventors: Ganesh Venkataraman; Viswanathan Sasisekharan; Ram Sasisekharan; Ratnaleela Bobba, all of Somerville; Charles L. Cooney, Brookline; Robert Langer, Newton, all of Mass.

[73] Assignee: Massachusetts Institute of Technology, Cambridge, Mass.

[21] Appl. No.: 261,166

[22] Filed: Jun. 17, 1994

[51] Int. Cl.$^6$ .............................. G06F 17/00; G06F 17/16
[52] U.S. Cl. ............................................. 364/496; 364/554
[58] Field of Search ................................ 364/505, 492, 364/550, 554, 571.01, 571.04, 496, 497; 376/245

[56] References Cited

U.S. PATENT DOCUMENTS

| | | | |
|---|---|---|---|
| 5,008,831 | 4/1991 | Feldman | 364/496 |
| 5,241,470 | 8/1993 | Lee et al. | 364/496 X |
| 5,249,137 | 9/1993 | Wilson et al. | 364/496 |
| 5,386,507 | 1/1995 | Teig et al. | 395/161 |
| 5,526,281 | 7/1996 | Chapman et al. | 364/496 |

OTHER PUBLICATIONS

Lang et al.; "Atomatic assignment of bond orders based on the analysis of the internal coordinates of molecular structures" Analytica Chimica acta, 1992, 265(2) 283–389.

Smith et al.; "Deriving 3–D representations of molecular structure from correction tables augmented with configuration designations using distance geometry."; Journal of Chemical Information and Computer Science; vol. 22, Issue 1 pp. 29–34 Feb. 1982.

Ivanon et al., "3DGen: a system for exhustine 3D moledular design proceeding from molecular topology;" Journal of Chemical Inf. and Comp. Science; vol. 34; Issue 2, pp. 234–243 Mar.–Apr. 1994.

Carhart et al., "CONGEN: an expert system aiding the structural chemist", Expert systems in the Micro–Electronic Age, Proceedings of the 1979.

Conrad, E. H. (1989) *Ann. N.Y. Acad. Sci*, 556, 18–28.; "Heparan Sulfate & Dermatan Sulfate".

Comper, W. D. (1981) *Heparin (And Related Polysaccharides)* Gordon & Beach, New York), Chapters 1–4, Apperdices 1 and 2.

Nicduszynski, 1, (1989) *Heparin.* eds. Lane, D. A. & Lindahl, U. (CRC Boca Raton FL), pp. 51–54.

Foster, M. J. & Mulloy, M. J. (1993) Biopolymers 33, 575–588.

Ramachandran G. N. & Sasisckharan, V. (1968) *Adv. Protein Chem.* 23, 283–437, Conformation of Polypeptides and Proteins.

(List continued on next page.)

Primary Examiner—Edward R. Cosimano
Assistant Examiner—Kamini Shah
Attorney, Agent, or Firm—Wolf, Greenfield & Sacks, P.C.

[57] ABSTRACT

A computer-implemented process determines candidate three-dimensional shapes of ring-shaped molecules through an exhaustive search of combinations of torsion angles of the bonds of the ring, given known bond lengths and bond angles for the bonds between atoms of the rings, a range of torsion angles and a resolution. Candidate combinations of the torsion angles are selected according to the range and resolution and coordinates of the atoms of the ring are determined for each candidate combination. It is then determined whether each candidate combination defines a physically possible ring. Indications of such candidate combinations are recorded. Candidate combination may then be selected from those recorded so that coordinates of atoms in candidate repetitive structures may be determined.

73 Claims, 7 Drawing Sheets

OTHER PUBLICATIONS

Chamberlian, L. N., Edwards, I.A.S., Stadler, H.P., Buchanan, J.G. & Thomas, W. A. (1981) *Carbohydr.* 90, The Conformation of Methyl 4.6-O(S)-benzylidene-2-choloro—2-deoxy-α-D-iodopyranoside in the Crystalline State and in Choloform Solution.

Scott, J. E. (1992) *FASEB J.* 6, 2639–2645,; Supermolecular organization of extracellular matrix glycosaminoglycans, in vitro and in the tissues.

Lindahl, U. (1989) in *Heparin*, eds. Lane, D. A. & Lindahl U. (CRC, Boca Raton, FL), pp. 159–183, Biosynthesis of heparin and related polysaccharides.

Fransson. L.-A. (1976) *Biochem. Biophys. Acta* 586, 179–188, Interactions between Dermatan Sulphate Chains, III.

Klagsburn, M. & Baird, A. (1991) Cell 67, 229–231.; "A Dual Receptor System is Required For Basic Fiberoblast Growth Factor Activity".

Varki, Ajit, "Biological Roles Of Oligosaccharides: All Of The Theories Are Correct," Glycobiology, vol. 3, No. 2, pp. 97–130 (1993).

Hiromu Sugeta and Tatsuo Miyazawa, "General Method For Calculating Helical Parameters Of Polymer Chains From Bond Lengths, Bond Angles, And Internal-Rotation Angles," Bipolymers, vol. 5, pp. 673–679 (1967).

Peter D. J. Grootenhuis, Constant A.A. vanBoeckel and Cornelius A. G. Haasnoot, "Carbohydrates And Drug Discovery-The Role Of Computer Simulation," Tibtech, Jan. 1994, vol. 12.

Alfred D. French and J. W. Brady, "Computer Modeling Of Carbohydrates, An Introduction," in Computer Modeling of Carbohydrate Molecules, eds. A. D. French et al. (Wash. D.C.: American Chem. Soc.), Chap. 1 pp. 1–19, 1990.

Igor Tvaroska, Cryrille Rochas, Francois-R. Taravel, and Tristan Turquois, "Computer Modeling Of Polysaccharide-Polysaccharide Interactions: An Approach To The -Carrageenan-Mannan Case," Bipolymers, vol. 32, 551–560 (1992).

Juan Ruiz, Manuel Lopez, Josefa Mila, Estrella Lozoya, Juan Jose Lozano and Ramon Pouplana, "QSAR And Conformational Analysis Of The Antiinflammatory Agent Amfenac And Analogues," Journal of Computer-Aided Molecular Design, vol. 7 (1993), pp. 183–198.

S. W. Homans and T. Rutherford, "Oligosaccharides And Recognition —A 'Shape' Problem Probed By N.M.R. And Molecular Modelling," Biochemical Society Transactions, vo. 21, pp. 449–552 (1993).

Harold J. Jennings, Andreze J. Gamian, and Fraser E. Ashton, "N-Propionylated Group B Meningococcal Polysaccharide Mimics A Unique Epitope On Group B Neisseria Meningitidis," J. Exp. Med. vol. 165, pp. 1207–1211 (Apr. 1987).

C. A. G. Haasnoot, "The Conformation Of Six-Membered Rings Described By Puckering Coordinates Derived From Endocyclic Torsion Angles," J. Am. Chem. Soc. 1992, 114, pp. 882–887.

Mulloy et al., "N.M.R. And Molecular–Modelling Studies Of The Solution Conformation Of Heparin," Biochem. J. (1993) vol. 293, pp. 849–858.

Erkki Ruoslahti and Yu Yamaguchi, "Proteoglycans As Modulators Of Growth Factor Activities," Cell, vol. 64, Mar. 8, 1991, pp. 867–869.

Lena Kjellen and Ulf Lindahl, "Proteoglycans: Structures And Interactions," Ann. Rev. Biochem. 1991, vol. 60, pp. 443–475.

Lubert Stryer, Biochemistry, 3rd Ed., Chap. 9, "Mechanisms Of Enzyme Action", pp. 203–210, New York: W. H. Freeman and Company.

Struther Arnott and W. E. Scott, "Accurate X–Ray Diffraction Analysis Of Fibrous Polysaccharides Containing Pyranose Rings. Part I. The Linked–Atom Approach," J.C.S. Perkin II, pp.324–335, 1972.

Yuko Inoue et al., "Conformational Equilibria of the L–Iduronate Residue in Non–Sulphated Di–, Tetra–And Hexa–Saccharides And Their Alditols Derived From Dermatan Sulphate," Biochem J. (1990) 265, pp. 533–538.

Giuseppe Gatti et al., "Resolution–Enhanced H–n.m.r. Spectra Of Dermatin Sulfate And Chondroitin Sulfates: Conformation of the Uronic Acid Residues," Carbohydrate Research, vol. 68. (1979) pp. C3–C7..

C. A. G. Haasnoot, et al., "The Relationship Between Proton–Proton NMR Coupling Constants and Substituent Electronegatives—I An Empirical Generalization of the Karplus Equations," Tetrahedron, vol. 36, (1980), pp. 2783–2792.

Dino R. Ferro et al., "Evidence For Conformational Equilibrium of the Sulfated L–Iduronate Residue in Heparin and in Synthetic Heparin Mono–and Oligosaccharides: NMR and Force–field Studies" J. Am. Chem. Soc. 1986, vol. 1008, pp.6773–6778.

Massimo Ragazzi et al., "A Force–Field Study of the Conformational Characteristics of the Iduronate Ring," Journal of Computational Chemistry, vol. 7, No. 2, (1986) pp. 105–112.

William T. Winter et al., "Solid–State 13C NMR and X–Ray Diffraction of Dermatan Sulfate," Biochemical and Biophysical Research Communications, vol. 137, No. 1, (1986) pp. 87–93.

A. K. Mitra et al., "Dermatan Sulfate: Molecular Conformations and Interactions in the Condensed State," J. Mol. Biol. (1983), 169, pp. 873–901.

Rees, D. A., et al. "Controversial Glycoaminoglycan Conformations," Nature, vol. 317 (1985), p. 480.

Casu, B. et al. "Controversial Glycoaminoglycan Conformations," Nature, vo. 322, (Jul. 1986), pp. 215–216.

Richard L. Jackson et al., "Glycosaminoglycans: Molecular Properties, Protein Interaction, and Role in Physiological Processes," Physiological Reviews, vol. 71, No. 2, (Apr. 1991), pp. 481–539.

COMPUTER-IMPLEMENTED PROCESS AND COMPUTER SYSTEM FOR ESTIMATING THE THREE-DIMENSIONAL SHAPE OF A RING-SHAPED MOLECULE AND OF A PORTION OF A MOLECULE CONTAINING A RING-SHAPED STRUCTURE

STATEMENT OF GOVERNMENT RIGHTS IN THE INVENTION

This work was supported by funds from the National Institutes of Health (GM 25810) and from the National Science Foundation. The United States government has certain rights in the invention.

FIELD OF THE INVENTION

This invention is related to the estimation of the three-dimensional shape of a chemical structure, in particular, ring-shaped molecules and molecules including a ring-shaped structure.

BACKGROUND OF THE INVENTION

Ring-shaped molecules are commonly found both in nature and in man-made compounds. In a ring-shaped molecule, the atoms forming the molecule are interconnected to each other to form a loop or ring, such as shown in FIG. 1. Viewed in two-dimensions, the distances between atoms, known as the bond lengths, and the angles formed at an atom and defined by its bonds with two other atoms, known as the bond angles, are well-known and can be readily determined experimentally. However, viewed in three-dimensions, these atoms may bond in a variety of rotations, identified by torsion angles. Accordingly, a ring-shaped molecule may have many shapes in three-dimensions. The term "shape" of a molecule signifies the arrangement, configuration or location of atoms forming the molecule with respect to each other in three-dimensions. In this field, shape is typically synonomous with "conformation." A "conformer" is a molecule with a particular shape. The shapes of ring-shaped structures are generally given descriptive names in the field of chemistry, such as a "boat", a "chair", a "sofa" or an "envelope." There are multitudes of other shapes.

Molecules including one or more ring-shaped structures are particularly common in biological systems. Most familiar, perhaps, are the carbohydrates in general and the simple sugars (monosaccharides) in particular. For example, the pyranose sugars have six-membered rings comprised of five carbon atoms and a single oxygen atom. These rings occur in the common monosaccharides (glucose, fructose, galactose and mannose) as well as their monosaccharide derivatives such as acetals (e.g., the glucosides), ethers (e.g., 2,3,4,6-tetramethylgluco-pyranose), and acids (e.g. glucuronic acid). The furanoses, a group of common sugars (e.g., arabinose or ribose) in which four carbon atoms and a single oxygen atom form a five-membered ring. Side groups (substituents) which may be attached to the atoms in these rings are essentially unlimited in number and may constitute the better part of the mass of the molecule (e.g., the gangliosides and nucleosides). More generally, ring-shaped structures including anywhere from three to dozens of atoms (e.g., porphyrins and other metalocycles) may be found in natural systems with a wide variety of side groups attached to The ring-shaped structures. In addition, the rings may contain heteroatoms, partial double, double or triple bonds (e.g. Phe, Tyr, dopamine, steroids, vitamins).

These ring-shaped structures are typically flexible and can shift between various three-dimensional shapes while in solution. The so-called "chair" and "boat" shapes of six-membered rings are the most famous examples in which rotation around the bonds forming the ring can cause the atoms to change their spatial orientation with respect to one another while still being constrained by the bonds of the ring. The flexibility of rings will, of course, decrease with decreasing ring size (e.g., cyclopropane) and with the number of double bonds, partial double bonds or triple bonds between the ring atoms (e.g., benzene and other cycloalkenes). In addition, the side groups on a ring may cause the ring preferentially or exclusively to assume a particular shape due to forces such as steric hindrance or electrostatic attraction or repulsion among themselves. Nonetheless, many ring structures of biological interest retain a great deal of flexibility.

Many biologically significant molecules have a structure which consists of a chain or polymer of many repeating subunits which include a ring-shaped structure. The most common examples are, again, the carbohydrates in general and the polysaccharides in particular. Cellulose and amylose, for example, each consist of a polymer of glucose rings joined by 1–4 glucoside linkages. More complex polymers with repeating disaccharide or oligosaccharide subunits and with a wide variety of side groups with varying complexity (e.g., glycoproteins, gangliosides, glycosaminoglycans and mucopolysaccharides) are also quite common. In addition, non-carbohydrates with repeating ring structures are also among the most important biological molecules known. For example, the backbone of the ribonucleic acids is a polymer of ribose rings which have purine or pyrimidine bases as side groups and which are linked by phosphate esters.

The three-dimensional shape of biologically active molecules is often as important or more important than their molecular composition. The active sites of enzymes and the binding sites of cell receptors and antigens in these molecules typically have a three-dimensional shape which is complementary to the shape of their substrates, ligands and antigens. Therefore, the function and selectivity of a portion of a given molecule is highly dependent upon its shape. This shape may be dependent on a ring-shaped structure in either the polymer backbone of the molecule or a side group of the molecule. The ability to understand and estimate these shapes is, therefore, often crucial to understanding the biological activity of many molecules. In addition, the rapidly developing field of rational drug design is based in large part upon the development of new molecules which mimic the shape of natural molecules, or portions thereof, but which have different reactivity. Competitive inhibitors of an enzyme, for example, typically have a similar shape and similar charge characteristics to the natural substrate but differ in molecular composition such that they may occupy the active site of an enzyme but are not subject to the chemical reaction which the enzyme normally catalyzes. A better understanding of the shape of molecules including one or more ring structures, therefore, is valuable both in assessing the three-dimensional structure of a natural molecule which is sought to be mimicked and in predicting the utility of a proposed mimic.

The carbohydrate chains of glycoproteins and proteoglycans are just now being recognized as being of immense biological importance. The importance of oligosaccharides is discussed in "Biological Roles of Oligosaccharides" by Ajit Varki in *Glycobiology*, Vol. 3, No. 2, pp. 97–130 (1993). These polymers of ring structures may be found bound to membrane proteins, bound to the extracellular matrix, as integral components of basement membranes, or as soluble components of the extracellular matrix. As they may have functions in cell recognition, cell adhesion, cell migration, antigen recognition, cytokine presentation or activation, immobilization of growth factors and enzymes, and clearance from circulation, these carbohydrates are now the subject of intense scrutiny and knowledge of their three-dimensional structure is greatly needed. Among those of greatest interest are glycosaminoglycans such as chondroitin-6-sulfate, dermatan sulfate, heparin, heparon sulfate, keratan sulfate, and hyaluronic acid, all of which are polymers of substituted pyranose disaccharides.

The importance of the shape of a ring-shaped molecule or of a molecule including a ring-shaped structure is not limited to biological environments. Such molecules also occur in synthetic polymers (e.g., cellophane and celluloid), paper (e.g., cellulose) and food (e.g., glucose). With respect to synthetic polymers, the properties of synthetic polymers depend on the interaction between each of the monomeric units of which it is comprised. Estimating the shape of one polymer molecule allows one to study the way a multiplicity of these polymers assemble in three dimensions and to determine bulk properties. Knowledge from such study also allows polymers to be designed to have specific properties. A better understanding of the shapes of such molecules, and the ability to predict the shape of newly proposed materials, such as synthetic polymers, remain critical needs.

There are some computer systems which are used to estimate the shape of a molecule which contains ring-shaped structures, but these systems all assume that each of the ring-shaped structures within the molecule takes some predetermined shape. An expert typically estimates this shape or configuration. Given the assumption by the expert that the ring-shaped structure has a particular shape or configuration, the shapes of chains of this structure are then examined using conventional techniques. Such methods are described, for example, by Grootenhuis, P. D. J., et al., in "Carbohydrates and Drug Discovery—the Role of Computer Simulation," *Tibtech*, January 1994 (Vol. 12), pp. 9–14; French, A. D., et al., in *Computer Moleling of Carbohydrate Molecules*, eds. French, A. D. and Brady, J. W. (Am. Chem. Soc., Washington, D.C.) pp. 1–19; and by Homans, S. W., et al., in "Oligosaccharides and Recognition—A 'Shape' Problem Probed By N.M.R. and Molecular Modeling," *Biochemical Society Transactions, Carbohydrates, Shapes and Biological Recognition*, Vol. 21, 1993, pp. 449–452.

SUMMARY OF THE INVENTION

The present invention seeks to meet the need for prediction or estimation of the three-dimensional shape of a ring-shaped molecule or a molecule including a ring-shaped structure. In one embodiment of the invention, candidate three-dimensional shapes of a ring-shaped molecule are determined by computer through an exhaustive search of the possible shapes of the ring, given known bond lengths and bond angles for the bonds between atoms of the rings. That is, for most structures of interest, there are few independently variable parameters (i.e., torsion angles). Given a range of interest and a desired resolution for each parameter, a search space thereby defined for combinations of these parameters can be exhaustively searched to determine which combinations define a ring. The combinations defining a ring can be further analyzed to estimate the three-dimensional shape of larger molecules, such as carbohydrates. By using an exhaustive search, all possibile shapes, given a range and resolution, are considered, Thus increasing the reliability of any analysis based on the shape estimated for the molecule in question.

One aspect of the invention is a process used in a computer-implemented process for estimating a shape of a molecule including a ring, from bond angles and bond lengths of the ring. The steps of the process, performed by a computer, include selecting candidate combinations of independently variable torsion angles according to a range of torsion angles and a resolution, determining coordinates of atoms defining the ring for each candidate combination, and recording an indication of each candidate combination which defines a physically possible ring.

Another aspect of the invention is part of a computer system for estimating a shape of a molecule including a ring from bond angles and bond lengths between the atoms of the ring. This part of the computer system includes means for selecting candidate combinations of independently variable torsion angles according to a range of torsion angles and a resolution, means for determining, for each candidate combination, coordinates of atoms defining the ring, and means for recording an indication of each candidate combination which defines a physically possible ring.

Another aspect of the invention is a programmed computer system which includes a memory element and a central processing unit. The memory element stores an identity of each atom, together with the bond angles and bond lengths between the atoms of the ring, and logic signals. The central processing unit accesses the memory to obtain the logic signals and uses them to operate as and to define both means for selecting candidate combinations of independently variable torsion angles according to a range of torsion angles and a resolution, means for determining, for each candidate combination, coordinates of atoms defining the ring, and means for recording an indication of each candidate combination which defines a physically possible ring.

Another aspect of the invention is part of a computer system for estimating a shape of a molecule including a ring, from bond angles and bond lengths of the ring. This part of the computer system includes a ring analysis module and a repetitive structure analysis module. The ring analysis module has an input for receiving the bond angles and bond lengths of the ring and identifies candidate combinations of independently variable torsion angles according to a range of torsion angles and a resolution. For each candidate combination, it determines coordinates of atoms defining the ring. It then records an indication of each combination which defines a physically possible ring, to provide a plurality of candidate ring shapes as an output. The repetitive structure analysis module is connected to the output of the ring analysis module and generates coordinates of atoms in candidate chains of the ring for each of the plurality of candidate ring shapes to provide candidate shapes of the molecule. These shapes are repetitive, such as a helix.

In another aspect of the invention, a computer system for estimating a shape of a ring of atoms, from a list of the atoms of the ring, bond angles and bond lengths defining the ring, includes first and second modules. The first module has an input for receiving a range and a resolution for independently variable torsion angles of the ring, and provides as an output a plurality of combinations of the torsion angles according to the indicated range and resolution. The second module has an input for receiving the output of the first module and the bond lengths and bond angles. In turn, this second module provides an output indicative of those combinations of torsion angles which define a physically possible ring.

Another aspect of the invention is a computer-implemented process for estimating a shape of a molecule including a ring-shaped structure. Such an estimation process employs a set of candidate shapes of the ring-shaped structure obtained from an exhaustive search of combinations of independently variable torsion angles. This process involves steps, performed by a computer, of generating coordinates of atoms in candidate chains of the ring-shaped structure for each of the plurality of candidate shapes. Selected candidate chains are screened against experimental data which indicate predetermined characteristics of the shape of the molecule. An indication of a candidate chain which matches the experimental data is recorded.

In another aspect of the invention, a computer system estimates a shape of a molecule including a ring-shaped structure. The system employs a set of candidate shapes of the ring-shaped molecule obtained from an exhaustive search of combinations of independently variable torsion angles of the ring-shaped structure. The computer system includes a memory element and a central processing unit. The memory element stores a representation of the set of candidate shapes of the ring-shaped structure, obtained from the exhaustive search, and logic signals. The central processing unit includes means for accessing the memory element to obtain the logic signals which are used such that the central processing unit defines means for generating coordinates of atoms in candidate chains of the ring-shaped structure for each of the plurality of candidate shapes.

In another aspect of the invention, a computer system estimates a shape of a molecule including a chain of a ring-shaped structure employing a set of candidate shapes of the ring-shaped structure obtained from an exhaustive search of combinations of independently variable torsion angles of the ring-shaped structure. The computer system includes both (a) means for receiving a plurality of candidate shapes from the set candidate shapes of the ring-shaped structure obtained from the exhaustive search, and (b) means for generating coordinates of atoms in candidate chains of the ring-shaped structure for each of the plurality of candidate shapes. In one embodiment, the system includes means for screening selected candidate chains against experimental data which indicate predetermined characteristics of the molecule.

Another aspect of the present invention is a computer-readable database of candidate shapes of a ring-shaped molecule developed by the process of estimating a shape of the ring-shaped molecule from bond angles and bond lengths of the ring-shaped molecule. This process includes identifying candidate combinations of independently variable torsion angles of the ring-shaped molecule according to a range of torsion angles and a resolution. For each candidate combination, coordinates of atoms in the ring are then determined. An indication of each candidate combination which defines a physically possible ring is stored in the database.

Another aspect of the invention is a computer system including a computer-readable medium, means for accessing information stored on the medium, and indications of candidate shapes of a ring of atoms stored on the medium and developed by a computer-implemented process of estimating a shape of a molecule including a ring, from an indication of atoms, bond angles and bond lengths of the ring. This process includes identifying candidate combinations of independently variable torsion angles of the ring according to a range of torsion angles and a resolution. For each candidate combination, coordinates of atoms defining the ring are determined. An indication of each combination which defines a physically possible ring is stored on the computer-readable medium in a manner to allow access using the indication of the atoms of the ring.

Another aspect of the invention is a computer-implemented process for using a computer-readable database of candidate shapes of a ring-shaped molecule prepared through an exhaustive search of combinations of independently variable torsion angles of the ring-shaped molecule, for estimating a shape of a molecule comprising the ring-shaped molecule. This process involves accessing the computer-readable database to retrieve one of the candidate shapes of the ring-shaped molecule. A computer is used to generate an estimate of the shape of the molecule comprising the ring-shaped molecule from the retrieved candidate shape. In one embodiment, the process is repeated so as to obtain multiple estimates.

These and other aspects of the invention will be better understood from the following detailed description.

DETAILED DESCRIPTION

The present invention will be more completely understood through the following detailed description which should be read in conjunction with the attached drawing in which similar reference numbers indicate similar structures. All references cited herein are hereby expressly incorporated by reference.

Because of the flexibility of ring structures, it is inappropriate to assume that a given ring structure has a single three-dimensional shape in all molecules in which it occurs. For molecules composed of many rings joined in a chain such an assumption is even more inappropriate. Errors in assumptions about the three-dimensional shape of each of the individual rings in a molecule are compounded in any of estimate of the three-dimensional shape of the entire molecule.

Figure 2:
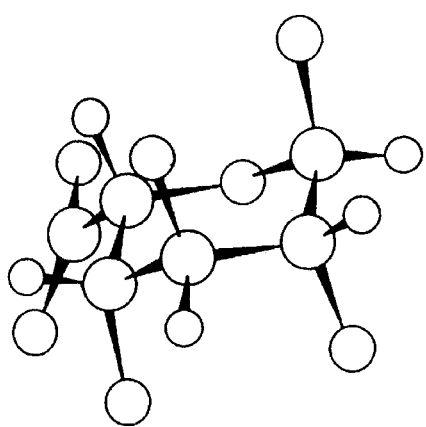
FIG. 2 is a diagram of the $^1C_4$ conformer which has been used to estimate the shape of heparin.
Figure 4:
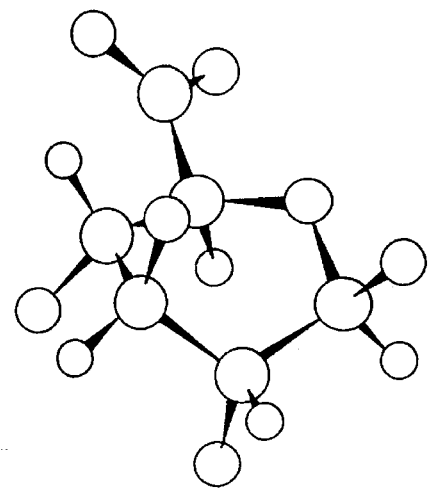
FIG. 4 is a diagram of the $^2S_0$ conformer which has been used to estimate the shape of heparin.
Figure 3:
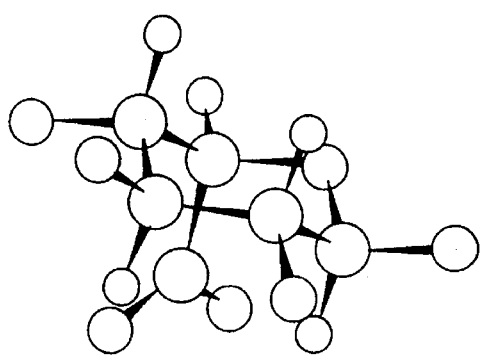
FIG. 3 is a diagram of the $^4C_1$ conformer which has been used to estimate the shape of heparin.
Figure 5:
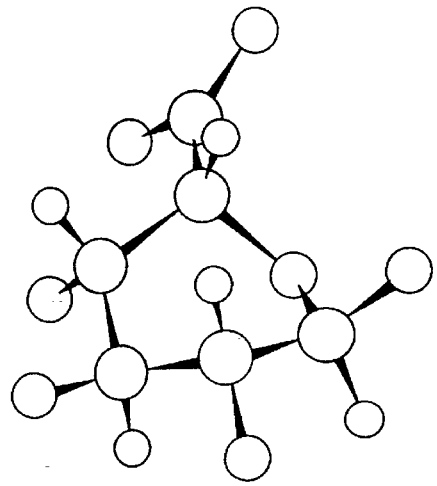
FIG. 5 is a diagram of the $^0S_2$ conformer which an analysis in accordance with this invention suggests should be used to estimate the shape of heparin.

In the prior art, an expert makes an assumption about the shape of a ring structure but does not exhaustively examine the possibilities and implications of alternative shapes of a ring-shaped structure. Thus, the shape of the ring-shaped structure selected by an expert may be inaccurate, thus causing disagreement and inaccurate analyses. For example, experts often disagree about the ring-shaped structures in heparin, thus causing disagreement about molecules containing this structure. In particular, as discussed in "Molecule and Mechanics and the Structure of Iduronate Containing Carbohydrates" by A. Rigazzi, et al., in *Computer Modeling of Carbohydrate Molecules*, eds. A. D. French et al. (Washington, D.C.: American Chemical Society, 1990), pp. 332–344, many experts have suggested that heparin is based on a molecule having a shape as shown in either of FIGS. 2, 3 and 4 which are commonly referred to, respectively, as the $^1C_4$, $^4C_1$, and $^2S_0$ conformers. From the results of use of this invention, we have found that the shape shown in FIG. 5 ($^oS_2$) is more accurate.

Little quantitative, analytical work has been done on the estimation of the three-dimensional shapes or conformations of ring-like, cyclic or closed molecular structures. The reason for this scarcity of prior work is that the problem of estimating the shape of a ring is complex, and involves solving a "ring closure" problem. That is, because a ring is a closed structure, the parameters defining its shape cannot be independently varied in a search for mathematically possible shapes. Also, there are too many mathematically possible shapes to test in a practical way each of them as a proposed shape of a molecule.

The present invention seeks to meet the need for prediction or estimation of the three-dimensional shape of a ring-shaped molecule or a molecule including a ring-shaped structure. In one embodiment of the invention, candidate three-dimensional shapes of a ring-shaped molecule are determined by computer through an exhaustive search of the possible shapes of the ring, given known bond lengths and bond angles for the bonds between atoms of the rings. For most structures of interest, there are few independently variable parameters (i.e., torsion angles). Given a range of interest and a desired resolution for each parameter, a search space thereby defined for combinations of these parameters can be exhaustively searched to determine which combinations define a ring. The combinations defining a ring can be further analyzed to estimate the three-dimensional shape of larger molecules, such as carbohydrates. By using an exhaustive search, one guarantees that all possibilities have been considered, thus increasing the reliability of an analysis based on the shape estimated for the molecule in question.

Figure 6:
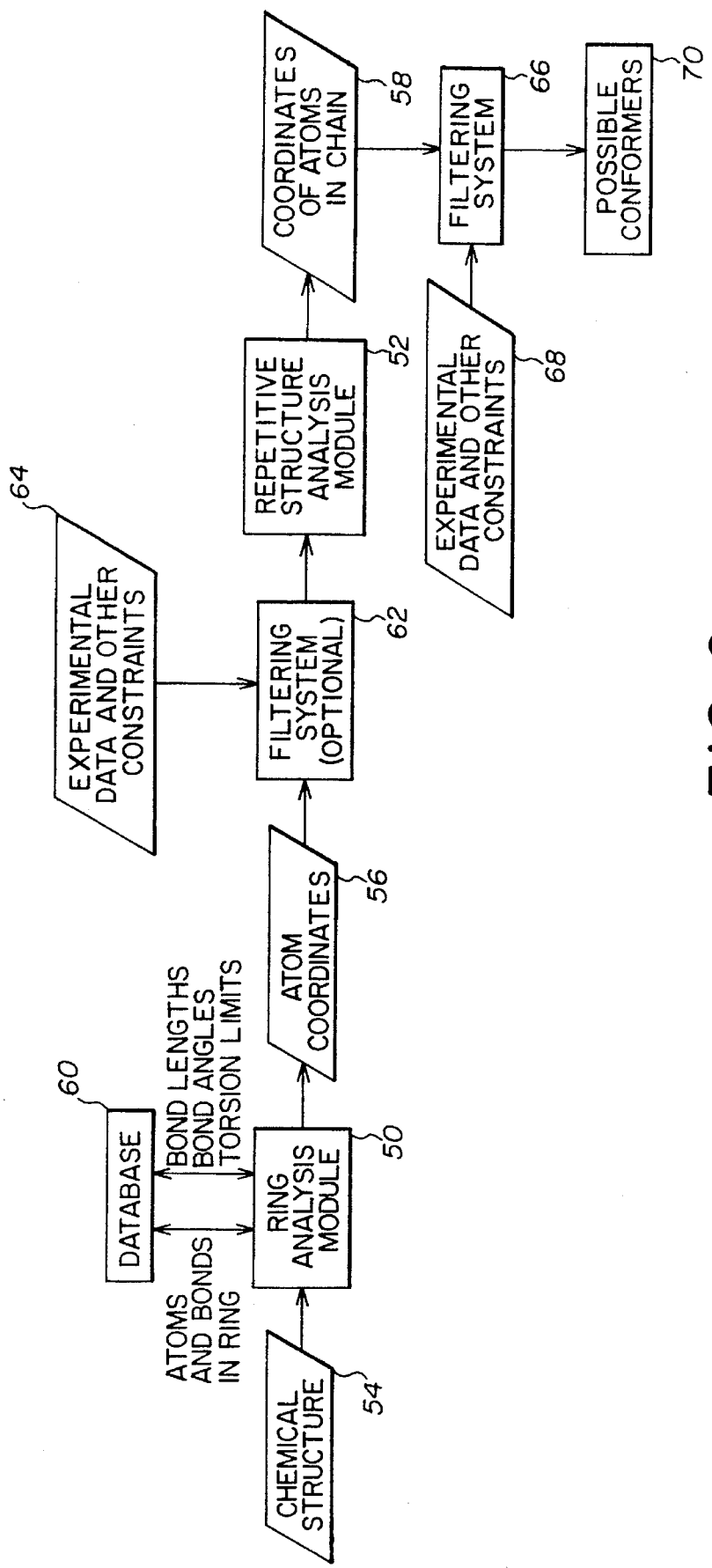
FIG. 6 is a block diagram of a system embodying the invention.

FIG. 6 shows a general block diagram of a system in accordance with the invention. The system includes a ring analysis module 50 which has an input which receives an indication of the chemical structure of a ring-shaped molecule to be analyzed, as indicated at 54. Based on the indication of chemical structure (i.e., the atoms and their order in the ring), the ring analysis module 50 obtains, preferably from a database 60, values for bond lengths, bond angles, and (optionally) torsion limits for the ring, based on the order of atoms in the ring. This database 60 is accessible according to the atoms and bonds found in the ring. The output of the ring analysis module 50 is a set of coordinates of the atoms 56, in some selected coordinate space, for each configuration in which it is possible for the atoms to form a ring. The coordinates are used by a repetitive structure analysis module 52, which generates coordinates of atoms in candidate chains of these rings. The output 58 of the repetitive structure analysis module 52 is thus, for each candidate chain of these rings, the coordinates of each atom in the chain.

The rings which may be analyzed using the present invention may include anywhere from four atoms to a number limited only by the computational ability and practical time-constraints of the computer system employed. For most applications, however, rings with four to fifty and, more typically, four to sixteen atoms are contemplated. The atoms which may be included in the rings are limited only in that they must be at least bivalent so that they may participate in the formation of a ring structure. Because they are common in biological molecules and synthetic polymers, the atoms carbon (C), oxygen (O), nitrogen (N), sulfur (S) and phosphorus (P) are preferably included in any embodiment and, more particularly, at least carbon, nitrogen and oxygen, Interposed between the ring analysis module 50 and the repetitive structure analysis module 52 is optionally a filtering system 62 which receives experimental data and other constraints 64 which indicate predetermined characteristics of a molecule. Filtering system 62 screens the candidate combinations output by module 50 against such data and constraints to eliminate some candidate shapes found by the ring analysis module 50. Such a reduction in candidate shapes prior to analysis using the repetitive structure analysis module 52 significantly reduces the number of possibilities to be processed by module 52. The output of repetitive structure analysis module 52 is applied to a similar filtering system 66 which also receives experimental data and other constraints 68, and screens the candidate chains and eliminates some of candidate shapes of the molecule in accordance with that information. Elimination by the filtering systems 62 and 66 can be performed by deleting candidates from the data file or by marking them in some way, such as by setting a bit in memory to indicate that they are not physically possible. The output of the filtering system 66 is a set of coordinates for each candidate shape 70 of the chemical structure analyzed.

The ring analysis module 50, the repetitive structure analysis module 52 and the filtering systems 62 and 66 can be implemented using a computer executing one or more suitable computer programs. The computer programs are typically embodied as logic signals stored in a memory which a processor reads and uses to perform various actions. The modules 50 and 52 and systems 62 and 66 may also be implemented using special purpose digital or analog electrical circuits, which are also essentially computers.

Figure 7:
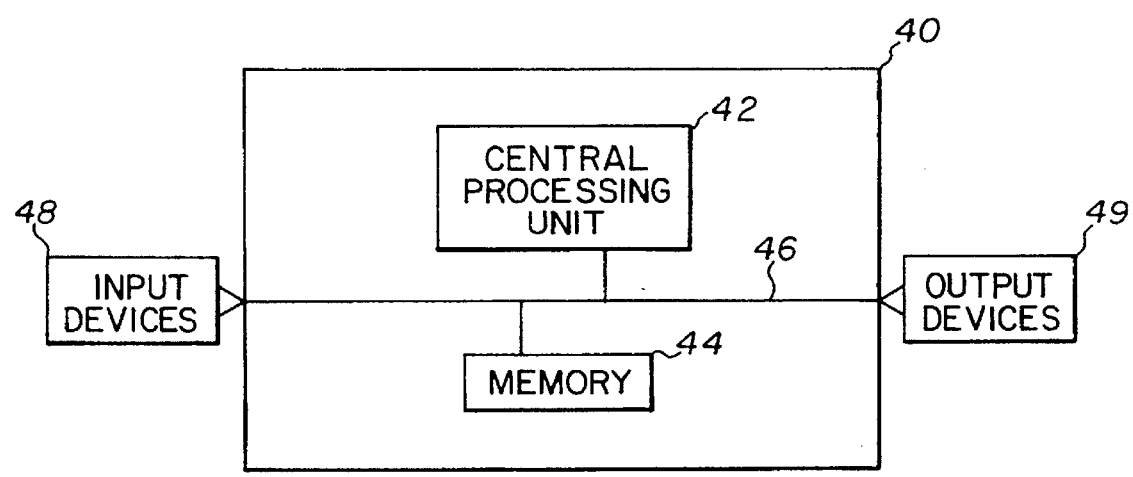
FIG. 7 is a block diagram of a computer suitable for implementing the present invention.

The computer is preferrably electrical, digital and programmable. A typical computer 40 suitable for implementing these programs is shown in FIG. 7. It is foreseeable that optical computers will become available with similar capabilities. This computer 40 includes a central processing unit 42 and a memory element 44 connected by a bus 46. The central processing unit 42 typically includes a microprocessor and supporting control logic. The memory element 44 is typically a volatile, random access memory, which may be either static or dynamic. The computer 40 also includes input devices 48 and output devices 49. The input device 48 may be a keyboard, a mouse, a trackball, a touchpad, or other type of input device for a computer, including a communication device. The output devices 49 include storage, display and communication devices. Display devices include video displays, such as liquid crystal displays (LCD's), cathode ray tube (CRT) displays, and other displays; storage devices include magnetic, optical and magneto-optical recording media, including disks and other non-volatile random access media, as well as tapes and other non-volatile linear access media; communication devices include networks and network interfaces, modems, and the like. These devices are commonly both input and output devices.

In one embodiment of the inventions, the applicant has implemented the ring analysis module 50 as a computer program using MATLAB (Version 4.1) high performance numeric computation and visualization software, available from The Math Works, Inc., of Natick, Mass., on a DECSTATION5000 computer manufactured by Digital Equipment Corp. of Maynard, Mass. A *Reference Guide*, a *User Guide*, an *External Interface Guide*, and on line help for version 4.1, all published by the Math Works, Inc. in August 1992, are available with this system to assist in program development.

The repetitive structure analysis module 52 has been implemented using a computer program written in the FORTRAN programming language. DEC Fortran Version 3.2 was used on a DECSTATION5000 computer. XL Fortran Compiler/6000 Version was used on a RS/6000 computer made by International Business Machines (IBM). This program is readily available and is based on "General Method for Calculating Helical Parameters of Polymer Chains from Bond Lengths, Bond Angles, and Internal-Rotation Angles" by H. Sugeta and T. Miyazawa, in *Biopolymers*, 1967, Volume 5, page 673. It was implemented as the "NANDH" computer program by N. Pattabiraman and is published in a Ph.D. thesis entitled *Conformation of Polynucleotides*, by N. Pattabiraman at the Indian Institute of Science, Bangalore, India, 1979. Version 3.1 of the NANDH computer program, released in October of 1992, is currently available from N. Pattabiraman at the Naval Research Laboratory in Washington, D.C. The NANDH computer program is preferably modified to automatically generate coordinates of a plurality of candidate chains for each of a plurality of candidate shapes of a basic ring structure. This modification involves conventional programming techniques. This program has a portion which reads a data file for its input of one candidate ring shape. Thus, it can readily be modified to repeat execution on different data files.

Each of the filtering systems 62 and 66 is preferably the commercially-available Insight II Version 2.3.0, Discover and Apex 3-D 1.4 computer programs, of the Molecular Modeling software package currently available from BIOSYM Technologies, of San Diego, Calif. These programs are commercially available for use on an IRIS computer workstation from Silicon Graphics, Inc. of Milpitas, Calif. One purpose of this software package is to add side groups to a basic backbone structure of a polymer to allow for further elimination of some configurations as possible conformations, by determining if there is steric hindrance.

The side groups which may be included are essentially unlimited, both chemically and theoretically, but may be limited in view of practical constraints on the computer system. Preferably, a database is provided with structural data on such common side groups as the radicals hydrogen (H—), methyl ($CH_3$—), ethyl ($CH_3CH_2$—), hydroxyl (HO—), methoxy ($CH_3O$—), ethoxy ($CH_3CH_2O$—), formyl (CHO—), acetyl ($CH_3CO$—), amino ($NH_2$—), sulfate ($SO_4$—), phosphate ($PO_4$—), adenine, thymine, guanine, cytosine and uracil (the purine and pyrimidine bases of common nucleic and ribonucleic acids), the halogens, and many others. This list is intended only to be illustrative and not exhaustive. In particular, the present invention may include any of a variety of databases, including data on any of a variety of classes of possible side groups. Indeed, for different applications (e.g. carbohydrate, nucleic acid, synthetic polymer structures), different databases may be provided or accessed. In addition a mechanism allowing the user to input the necessary data for any given side group may be included. Other information that may be used by filtering systems 62 and 66 is experimental data regarding the molecule, such as NMR, proton coupling constants, fiber diffraction length, side group accessibility for chemical modification, etc.

The various bond lengths and bond angles to be used in connection with the present invention are available in a database 60. A suitable database 60 is the Cambridge Structural Database, a database of machine-readable compilation, of experimental results on three-dimensional molecular structures. The Cambridge Structural DaTabase is maintained by the Cambridge Crystallographic Data Center (CCDC), in Cambridge, United Kingdom. It can be accessed using computer programs available from the CCDC by contacting either the Medical Foundation of Buffalo, Inc., or from CCDC directly. The values for bond lengths and bond angles may also be obtained experimentally, or from other sources, such as published articles. Thus, in a preferred embodiment, a database 60 is provided which includes typical bond lengths and bond angles for common bonds such as C—C, C=C, C—O, C=O, C—N, C=N, C—S, C—P and N—O. Again this list is not intended to be exhaustive and a mechanism may be provided for the user to input any bond lengths and bond angles which are not available from database 60. Furthermore, bond lengths and bond angles may be influenced by atoms which are adjacent to or substituted upon the atoms defining a given bond. Thus, for example, the C—C bond length of $CH_3CH_3$ will differ from that of $CH_3CHCl_2$ because of the chlorine substitutions for hydrogen. Atoms further removed, however, will have a far less significant effect and thus, for example, the C—C bond length of $CH_3CH_2R$ is likely to differ as R is changed from H— to $CH_3$— but is likely to differ only insignificantly as R is changed from $CH_3$— to $CH_3CH_2$—. Therefore, in another preferred embodiment, database 60 is expanded to include bond lengths and bond angles which take into effect adjacent atoms and substitutions. in particular, the adjacent atoms and substituents to be considered preferably include H—, alkyl, hydroxyl, alkoxyl, ketyl, amine, sulfyl, phosphyl and halogen.

Figure 1:
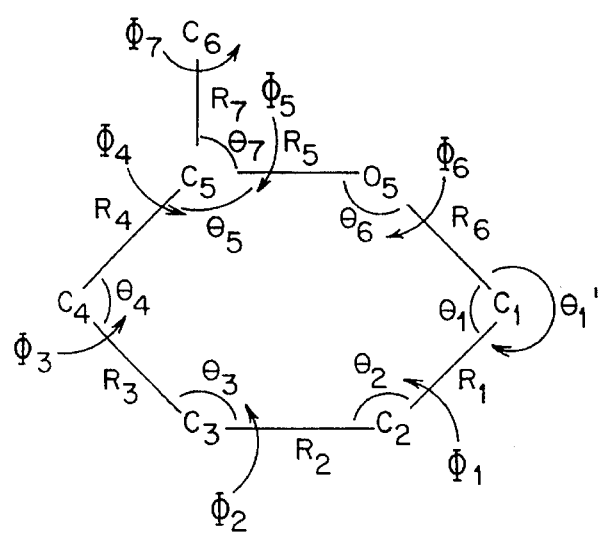
FIG. 1 is an illustration of a ring-shaped chemical structure.
Figure 8:
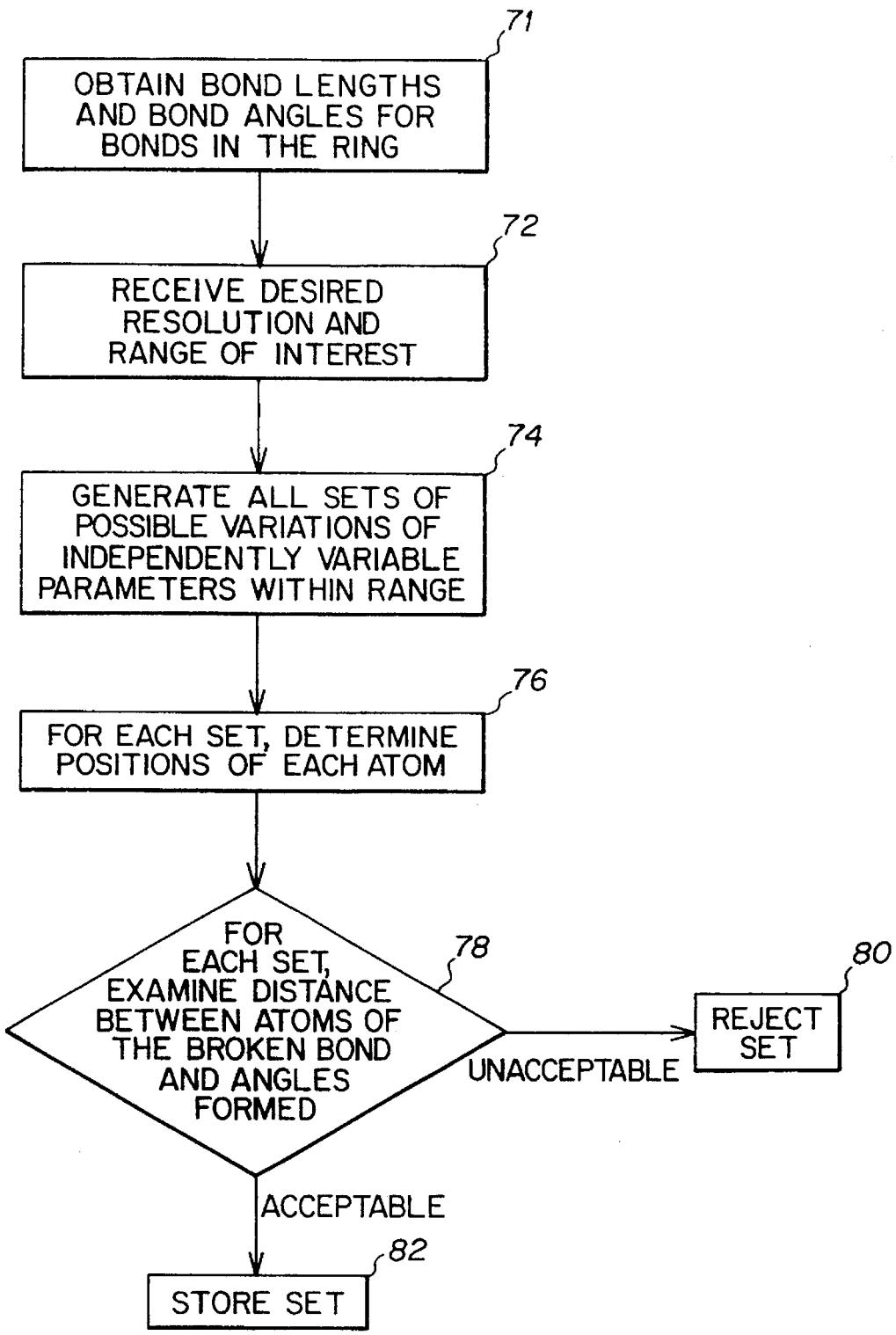
FIG. 8 is a flow chart describing the general process of the ring analysis module as shown in FIG. 6.
Figure 9:
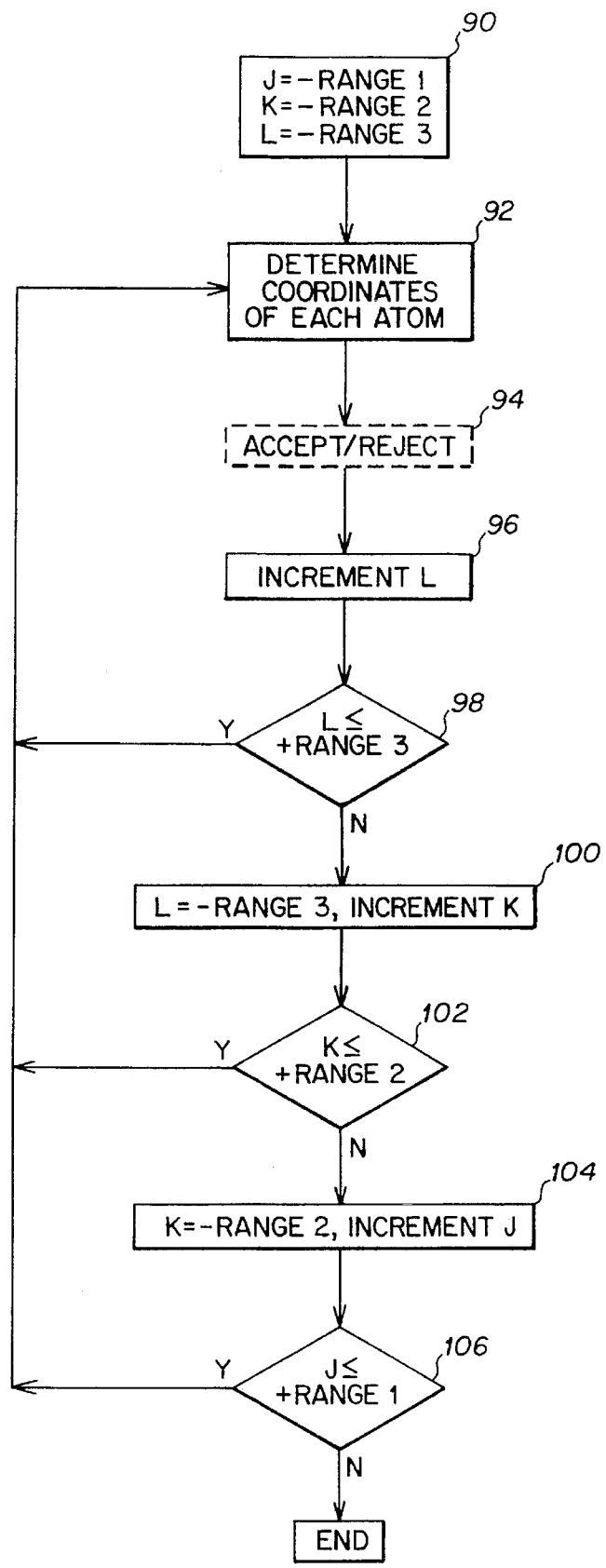
FIG. 9 is a flow chart describing in more detail the process of FIG. 8.
Figure 10:
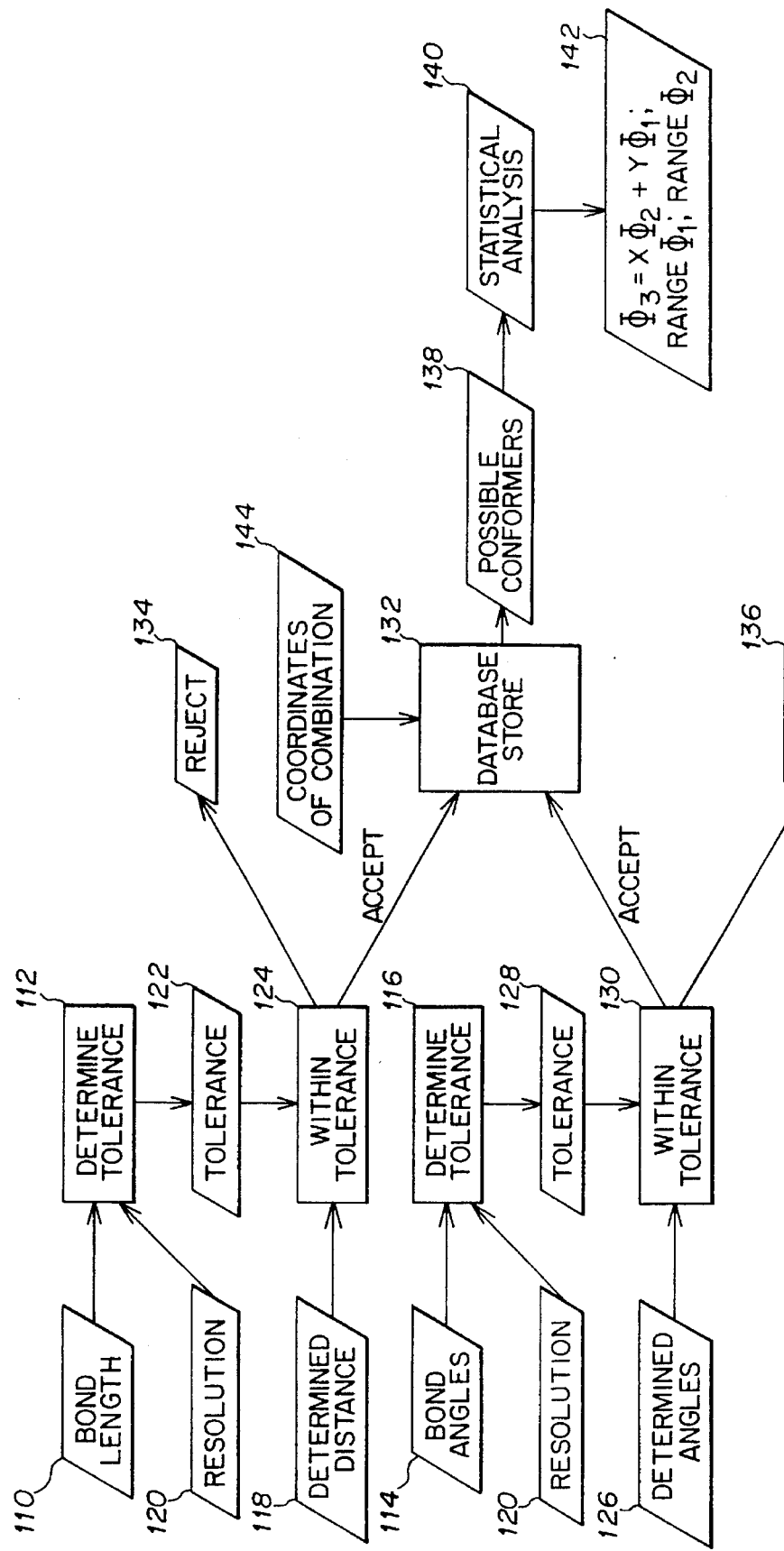
FIG. 10 is a data flow diagram describing in more detail the process of by which a candidate combination is accepted or rejected as a possible conformation to a ring structure.

A more detailed description of the ring analysis module 50 will now be provided in connection with FIGS. 8–10. FIG. 1, discussed above, shows a typical six-member ring including five carbon atoms C1–C5 and one oxygen atom O5. By convention, the bond length between C1 and C2 is referred to as R1. The bond angle formed by the bonds among O5, C1 and C2 is referred to as el and the torsion angle (or internal-rotation angle) of the bond from C1 to C2 is referred to as $\phi_1$.

The first step in determining candidate shapes of such a ring is obtaining the bond lengths and bond angles for the bonds in the ring as shown in step 71 in FIG. 8. This step is preferably performed by using some form of database, e.g., database 60, as this kind of information is well-known in the art of chemistry. Sometimes this information is found only in the literature and not in a database and, in that case, should be incorporated into the computer program or otherwise input by a user. For example, if a database access fails, a user could be prompted by the computer to input the information. Next, in step 72, the desired resolution and range of interest for the possible torsion angles is then received. For example, the torsion angles which may be varied in a search may be varied in increments of, e.g., 5°, from −80° to 80°. The increment value (i.e., step size) and the range are dependent on the number of candidate shapes which one desires to find as well as physical limits. For example, there are no reported cases of torsion angles within a six-member carbon and oxygen ring wherein the torsion angles have an absolute value greater than 80°. It is possible to set the entire range from −180° to 180° for the sake of completeness; however, many unnecessary searching steps would be performed.

It should be noted that some computer systems have different conventions concerning angle measurements. For example, as shown in FIG. 1, angle Θ1' is the actual angle, measured in radians, which should be used with the computer mentioned above, and is computed by calculating Θ1'=−(180−Θ1)*pi/180.

Given a desired resolution and range of interest for the torsion angles, and the bond lengths and bond angles for bonds in the ring, candidate combinations of independently variable torsion angles within the desired range at the desired resolution are then generated in step 74. The candidate combinations of independently variable torsion angles define a search space. For each candidate combination, the actual coordinates of each atom are then determined in step 76. For each of these sets, the distance between atoms of a broken bond (defined below) and the bond angles which form the broken bond are then determined in step 78. If this distance and these bond angles are determined to be unacceptable, as will be described below, the combination is rejected in step 80. Otherwise, the set is accepted as a candidate shape of the ring and an indication of the candidate combination is stored in step 82.

In the process defined by steps 74, 76 and 78, there is typically one bond which is assumed to be broken for performing the search so that all other parameters may be varied independently. After coordinates for the atoms for one combination are determined, it is then determined whether the coordinates of the atoms of the broken bond are such that the bond between them is likely to be physically possible, such that the candidate combination defines a physically possible ring. In the embodiments described below, the Torsion angles Φ1,Φ2 and Φ3 are varied. Therefore, the bond C5—O5 is broken. That is, the bond length R5 and bond angles Θ5 and Θ6 are not taken into consideration in the calculation of the atom coordinates in step 76. Then, in step 78, it is determined whether the determined positions for C5 and O5 are such that the bond length and bond angles thereby defined are within some acceptable range of the expected bond lengths and bond angles as determined in step 70. This process will be discussed in more detail below in connection with FIGS. 9 and 10.

FIG. 9 illustrates in more detail the overall process of steps 74 through 78 of FIG. 8. In more detail, the first step is setting variables, e.g., J, K and L, to be one of the limits of the ranges defined for each of the torsion angles to be varied, e.g., $\Phi_1$, $\Phi_2$ and $\Phi_3$ (step 90). Next, the coordinates of each atom, given the currently selected values of J, K and L for torsion angles Φ1, Φ2 and Φ3, are then determined in step 92. More details about this determination are discussed below. After the coordinates are ascertained, it is then determined in step 94 whether the resulting arrangement is acceptable. Alternatively, this step 94 may be performed after coordinates of each atom are determined for each combination (i.e., after step 106). Next, in step 96, one of the varied torsion angles is then incremented. If the torsion angle is still within the range as determined in step 98, processing returns to step 92 for determining coordinates. Otherwise, processing continues as step 100 by resetting variable L to its original lower limit range and one of the other torsion angles, e.g., K, is then incremented. It is then determined in step 102 whether K is still within the range defined. If it is, processing returns to step 92. Otherwise, K is reset to its original value in step 104 and J is incremented. If J is within the range as determined in step 106, processing again continues with step 92, otherwise, the process ends. At this stage, all of the candidate shapes of the ring have been obtained through an exhaustive search of the search space.

The process of determining the coordinates of each atom will now be described. The following notation will be used for this discussion. Note that the notation used is clockwise. If desired, counter-clockwise rotation may be used. "th" is a vector of the known bond angles. By convention, the bond angle about C1 is the first element of the vector; the bond angle about O5 is the last element of the vector. Similarly, "ph" is a vector of the torsion angles. By convention, the torsion angle of C2 with respect to C1 is the first element of the vector. The torsion angle of C1 with respect to O5 is the last element of the vector. th[x] represents the xth element of the vector th. ph[x] represents the xth element of the vector ph. The bond lengths are stored as a matrix R, where the first row of the matrix includes the bond lengths. Two more rows follow, of all zeros. R[:,x] represents the xth column of matrix R, and therefore is a vector. The first column of matrix R includes the bond length between C1 and C2; the last column of matrix R includes the bond length between O5 and C1.

T(x) is the matrix $$\begin{vmatrix} \cos(x) & -\sin(x) & 0 \\ \sin(x) & \cos(x) & 0 \\ 0 & 0 & 1 \end{vmatrix}^{-1}$$

P(X) is the matrix $$\begin{vmatrix} 1 & 0 & 0 \\ 0 & \cos(x) & -\sin(x) \\ 0 & \sin(x) & \cos(x) \end{vmatrix}^{-1}$$

To determine the coordinates of each atom in x,y,z Cartesian coordinates represented as a vector (0,0,0), an origin is first selected. For example, C3 could be established as the origin. Its coordinates LOC3 are thus the vector (0,0,0). Coordinates of some other points are then well-defined according to well-known coordinate transformation relations (e.g., T(x) and P(x)). Thus, the coordinates LOC2 of C2 are R[:,2]. The coordinates LOC1 of C1 are:

$$T(th[2])*R[:,1]+LOC2 \tag{1}$$

In equation (1), (as well as equations (2)–(6) below) each of the addends is a vector; hence, the sum is a vector.
The coordinates LOCO5 of O5 are $$T(th[2])*P(ph[1])*T(th[1])*R[:,6]+LOC1 \tag{2}$$

The coordinates LOC4 and LOC5 of C4 and C5 are then determined using C1 as the origin; these coordinates are then converted back to the original basis where C3 defined the origin. With C1 as the basis, the coordinates LOC41 of C4 are:

$$T(-th[2])*P(-ph[2])*T(-th[3])*R[:,3]+T(-th[2])*R[:,2]+R[:,1] \tag{3}$$

The coordinates LOC51 of C5 with C1 as the basis are:

$$T(-th[2])*P(-ph[2])*T(-th[3])*P(-ph[3])*T(-th[4])*R[:,4]+LOC41 \tag{4}$$

The coordinates LOC41 and LOC51 are converted back to the original basis of C3 using the following formula:

$$LOC4=R[:,2]+T^{-1}(-th[2])*(-LOC41+R[:,1]) \quad (5)$$

$$LOC5=R[:,2]+T^{-1}(-th[2])*(-LOC51+R[:,1]) \quad (6)$$

Because the set of x,y,z coordinates LOC1, LOC2, LOC3, LOC4, LOC5, and LOCO5, can be determined using R, th, ph[1], ph[2], and ph[3], these parameters (i.e., R, th, ph[1], ph[2], and ph[3]) fully define a six member ring or closed structure. Instead of calculating the set of Cartesian coordinates, a set of spherical coordinates may also be calculated, according to the following equations.

$$ph[4]=f(LOC3,LOC4,LOC5,LOCO5); \quad (7)$$

$$ph[5]=f(LOC4,LOC5,LOCO5,LOC1);$$

$$ph[6]=f(LOC5,LOCO5,LOC1,LOC2);$$

where f(w,x,y,z) is a value q which results from the execution of the following functions:

$$a=x-w$$

$$b=x-x$$

$$c=x-y$$

$$d=z-z$$

$$ac=\text{cross}(a,c)$$

$$cd=\text{cross}(d,c)$$

$$\text{cost}=(ac'*cd)/(sqrt(\text{sum}(ac.\hat{}2))*sqrt(\text{sum}(cd.\hat{}2)));$$

$$q=a\cos((\text{cost}))*180/pi;$$

The step of accepting and rejecting a combination of torsion angles as a candidate shape as shown in steps 78 and 94 will now be described in connection with FIG. 10. FIG. 10 is a data flow diagram describing this process. Given the bond lengths 110 of the broken bond, e.g., RS, and the desired resolution 120, a tolerance can be determined as shown at 112. Similarly, given the bond angles about the broken bond, such as Θ5 and Θ6 (114), and the resolution 120 a tolerance for the angles can be determined as shown at 116. The determined distance between the atoms defining the broken bond as shown at 118 are then compared with the determined tolerance 122 as shown at 124. The determined bond angles about the broken bond as shown at 126 are then compared with the determined tolerance 128 for the bond angles as indicated at 130. If both the bond length and bond angles determined for a given combination are within the determined tolerances, the coordinates of the combination 144 are stored in a computer-readable database 132. Otherwise, the combination is rejected as shown at 134 and 136.

The computer-readable database 132 preferably includes a computer-readable medium, such as memory element 44, but preferably an output device 49, such as a non-volatile storage device. It also includes means for accessing the information sorted therein; preferably, candidate combinations are accessible using an indication of the atoms defining the ring. When the database 132 is accessed by the central processing unit L(CPU) 42, the CPU copies the data into memory element 44.

If all of the candidate combinations of independently variable torsion angles have been analyzed and the candidate shapes have been stored in a computer-readable database 132, the candidate shapes 138 can be applied to a statistical analysis module 140. This statistical analysis may be linear regression to fit the stored coordinates of the candidate shapes to an equation which represents one of the independently varied parameters, e.g., Φ3, as a function of the others, e.g., Φ1 and Φ2. With 6-member rings, such a regression always results in a linear function in the form Φ3=xΦ2+Φ1. Also, the torsion angles $\Phi_1$, $\Phi_2$ and $\Phi_3$ of the candidate shapes define the ranges in which Φ1 and Φ2 can then be varied. The equation and ranges are indicated at 142 in FIG. 10. Given this equation and the resulting ranges, steps 94, 96, 98 and 100 can be eliminated (except for the increment K portion of step 100) and the range values as determined in step 90 can be replaced. The elimination of step 94 is possible because $\Phi_3$ is automatically determined from $\Phi_1$ and $\Phi_2$ and the ring is known to close in the ranges of $\Phi_2$ and $\Phi_1$ which are used. These constants are independent of the resolution used to generate the original data and can thus be used to analyze the ring structure at a significantly finer grain. That is, the search space may be reduced and can be searched using a smaller resolution. The results of the search, more candidate combinations, can also be stored in the computer-readable database 132.

As a specific example, the Applicant has analyzed a monomer for a six-member sugar. The bond lengths $R_1$ through $R_6$ are respectively 1.522, 1.521, 1.524, 1.525, 1.436 and 1.429 angstroms. The bond angles used for Θ1–Θ6 are respectively 109.4, 110.6, 110.3, 110.2, 110.2 and 112.3 degrees. The tolerance for R5, as determined in step 112, in this example was from 1.35 to 1.65 angstroms. The tolerance for Θ5 was 105.2° to 120.2° and for Θ6 was 105.0° to 120.0°. In this case, Φ3=0.87*Φ1+1.72* Φ2 where $\|\Phi_1\|+\|\Phi_2\|>40°$. Thus, the search space is reduced and the ring analysis module can be re-executed using the smaller range, the equation relating $\Phi_3$ to $\Phi_2$ and $\Phi_1$, and a smaller resolution.

Other rings may also be analyzed using this system, with minor modifications. For example, as shown in FIG. 6, a ring may also have an additional carbon atom C6 attached, for example to C5 In this case the torsion angle $\Phi_7$, bond angle $\Phi_7$ and bond length $R_7$ are well-known. Therefore, the coordinates of C6 can be readily determined.

Similarly, five-member rings are also common. In such a case, there are only two independently variable parameters rather than three (e g. $\Phi_1$ and $\Phi_2$). Thus the procedure is relatively the same, merely requiring the elimination of steps which vary the unused variable parameter (e.g., L). Also, in the statistical analysis 134 and the resulting equation and range 136 reduce the problem to one independently variable parameter.

This system may also be used to analyze rings with seven or more members. In such cases, the number of independently variable parameters increases linearly. Thus, seven member rings involve a search using four independently variable parameters. With statistical analysis after an initial determination of candidate shapes, the search for seven-number rings is reduced to require three independently variable parameters.

Figure 11:
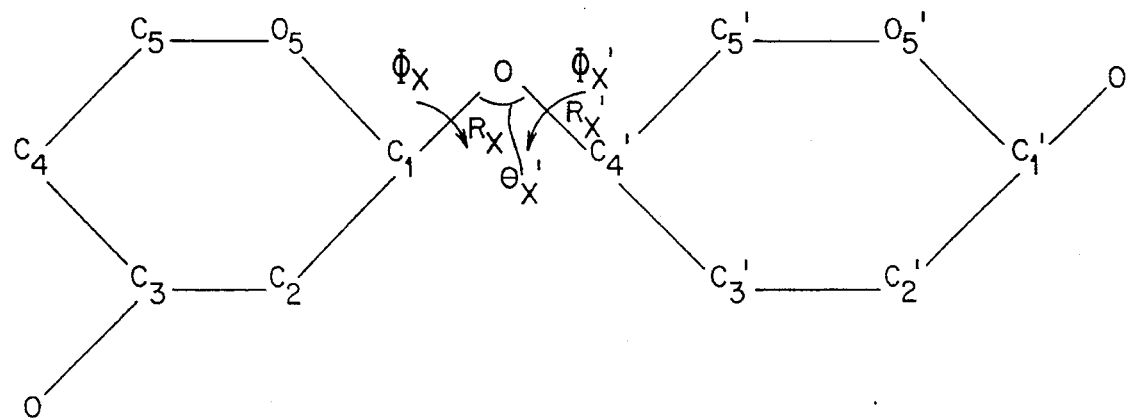
FIG. 11 is an illustration of the chemical structure of a monomer comprised of two ring subcomponents.

It is also possible that a chemical compound to be analyzed is an asymmetric unit comprised of two rings, such as shown in FIG. 11. In FIG. 11, this structure includes one ring defined by C1 through C5 and O5 and a second ring defined by C1' through C5' and O5'. These two rings are interconnected via a bond to an oxygen atom O between C1 and C4'. The chemical structure is then composed of chains of these monomers between C1' of a first monomer and C3 of a second monomer via another oxygen bond. In such cases, each of the two rings is analyzed separately. Then, the different combinations resulting from a connection between the candidate shapes of these rings are then determined where the linkage torsion angles ΦX and ΦX' are independently variable parameters. The bond lengths X and X' and bond angle ΘX' are well-known. The coordinates of the atoms in each of the possible variations of ΦX and ΦX' are then determined. For example, ΦX may be varied from 0 to 360 degrees over 10 degree intervals, resulting in 1296 combinations. After some preliminary analysis to eliminate part of the initial range, a smaller range and smaller step size may then be used. For each of these combinations, a distance matrix is then calculated, indicating the distance from each atom to each other atom in the combination. If any of these distances is less than a physically acceptable limit, the combination is rejected.

Given any of the candidate shapes to the basic ring structure analyzed using such an exhaustive search, these possibilities can be applied to the optional filtering system 62 and the repetitive structure analysis module 52 can then be used to generate candidate chains of these candidate shapes, as discussed above in connection with FIG. 6. It should be understood that this analysis may still result in a large number of candidate shapes for a molecule. However, this number can be reduced using the filtering systems 62 and 66 and by grouping those elements with related properties (i.e. active side groups in the same locations, It should be evident that the ring analysis module 50, due to its generality, may be used to analyze a variety of shapes of a small number of ring-shaped components, thus generating a database of these candidate shapes as shown at 132 in FIG. 10. Such a database may be used to analyze a larger number of structures such as carbohydrates which include these basic structures, using the other modules of the system identified in FIG. 6. In particular, the repetitive structure analysis module 52 may access database 132, which may be connected to the same computer 40 or to another computer via a communication device (one of the input devices 48 and output devices 49).

Some aspects of the filtering systems 62 and 66 may also be combined in the ring analysis module 50. For example, the effect of side groups on the bond lengths and bond angles may be accounted for by adjusting the values used for these lengths and angles. In such a case, the ring analysis module 50 probably should not be used for generating a generic database. Nonetheless, the effects of these side groups may be negligible with respect to the resolution used either in the search or by the computer system for the calculations required.

Data concerning the structure of such molecules is useful in molecular modeling, rational drug design, studies of chemical reactivity, derivation of force fields, and the examination of hydrogen-bonded and non-bonded interactions that govern molecular recognition phenomena. For example, new molecules can be designed, including drugs, which mimic the shape of more complex molecules such as carbohydrates. The methodology for designing such molecules is described, for example, in "The Computer Program LUDI: A new Method for the DeNovo Design of Enzyme Inhibitors" by H. -J. Bohm, in the *Journal of Computer-Aided Molecular Design*, Vol. 6, pp. 61–78 (1992). Such methodologies are embodied in computer programs which are commercially available, such as LUDI, part of the three-dimensional graphical modeling system mentioned above and which is available from Biosym Technologies. Also, computer programs are available from the Cambridge Crystallographic Data Center, known as the Cambridge Structural Database (CSD) software. Which is able to search for structures with geometric parameters selected within chosen ranges. For example, one can take a structural fragment from one molecule and identify other molecules which have similar fragments.

Given this description of a few embodiments of the invention, it should be apparent to those skilled in the art that the foregoing detailed description is merely illustrative and not limiting, having been presented by way of example only. Numerous modifications and other embodiments are within the scope of one of ordinary skill in the art. For example, this system can readily be modified to analyze molecular structures having two or three rings with common bonds, such as napthalene. These and other modifications are contemplated as falling within the scope of the invention as defined by the appended claims.

What is claimed is:

1. In a computer-implemented process for estimating at least one shape of a molecule including a ring of atoms, from bond angles and bond lengths of the ring defined by the atom of the ring, a process comprising the steps, performed by a computer, of:

selecting a candidate combination of values for independently variable parameters of the ring of atoms;

selecting first and second adjacent atoms of the ring wherein the first and second atoms define a broken bond;

for the selected candidate combination, determining coordinates of the atoms of the ring in a sequence from the first atom to the second atom according to the bond angles, the selected candidate combination of values, and the bond lengths;

comparing a distance between the determined coordinates of the first and second atoms of the ring to an acceptable range of a bond length of the broken bond between the first and second atoms to determine whether the determined coordinates define a physically possible ring; and recording an indication of the candidate combination as a candidate shape if the determined coordinates define a physically possible ring.

2. In a computer system for estimating at least one shape of a molecule including a ring of atoms, from bond angles and bond lengths defined by the atoms of the ring, a system comprising:

means for identifying a candidate combination of values for independently variable parameters of the ring of atoms;

means for selecting first and second adjacent atoms of the ring, wherein the first and second atoms define a broken bond;

means for determining, for the selected candidate combination, coordinates of the atoms of the ring in a sequence from the first atom to the second atom according to the second angles, the selected candidate combination of values, and the bond lengths;

means for comparing a distance between the determined coordinates of the first and second atoms of the ring to an acceptable range of a bond length of the broken bond between the first and second atoms to define whether the determined coordinates define a physically possible ring; and means for recording an indication of the candidate combination as a candidate shape if the determined coordinates define a physically possible ring.

3. In a computer system for estimating at least one shape of a molecule including a ring of atoms, from bond angles and bond lengths defined by the atoms of the ring, a system comprising:

(a) a memory element for storing information including an identity of the atoms, the bond angles and the bond lengths, and logic signals;

(b) a central processing unit connected to the memory element and including means for accessing the memory element to read the logic signals such that the central processing unit defines:

(i) means for identifying a candidate combination of independently variable parameters of the ring of atoms;

(ii) means for selecting first and second adjacent atoms of the ring, wherein the first and second define a broken bond;

(iii) means for determining, for the selected candidate combination, coordinates of the atoms of the ring in a sequence from the first atom to the second according to the bond angles, the selected candidate combination of values, and the bond lengths;

(iv) means for comparing a distance between the determined coordinates of the first and second atoms of the ring to an acceptable range of a bond length of the broken bond between the first and second atoms to determine whether the determined coordinates define a physically possible ring; and (v) means for recording an indication of the candidate combination as a candidate shape if the determined coordinates define a physically possible ring.

4. In a computer system for estimating at least one shape of a molecule including a ring of atoms, from bond angles and bond lengths defined by the atoms of the ring, a system comprising:

a ring analysis module having an input for receiving the bond angles and the bond lengths and which identifies a plurality of candidate combinations of values for independently variable parameters of the ring of atoms and which determines, for each identified candidate combination, coordinates of atoms according to the bond lengths, bond angles and the identified candidate combination of values, to provide as an output an indication of a plurality of candidate ring shapes when the determined coordinates define a physically possible ring; and a repetitive structure analysis module connected to the output of the ring analysis module and providing as an output a candidate shape of a chain of each of the candidate ring shapes of the physically possible ring.

5. In a computer system for estimating at least one shape of a molecule including a ring of atoms, from bond angles and bond lengths defined by the atoms of the ring, a system comprising:

a first module having an input for receiving a range and a resolution for independently variable parameters of the ring of atoms, and which provides as an output a plurality of candidate combinations of values for the independently variable parameters: and a second module having an input for receiving the output of the first module and the bond lengths and bond angles of the atoms of the ring and which provides an output indicative of candidate combinations of values for the independently variable parameters from the plurality of candidate combinations output by the first module which define a physically possible ring, wherein the second module includes means for comparing a distance between determined coordinates of at least two of the atoms of the ring to an acceptable range of a bond length between the at least two atoms to determine whether the determined coordinates define a physically possible ring.

6. In a computer-implemented process for estimating at least one shape of a molecule including a ring-shaped structure from a set of candidate shapes of the ring-shaped structure obtained from an exhaustive search of combinations of independently variable torsion angles of the ring-shaped structure, a process comprising the steps, performed by a computer, of:

generating coordinates for atoms in a candidate chain of the ring-shaped structure, for each candidate shape in the set of candidate shapes;

screening each candidate chain against experimental data which indicate predetermined characteristics of the shape of the molecule; and recording an indication of each candidate chain which matches the experimental data.

7. In a computer system for estimating at least one shape of a molecule including a ring-shaped structure from a set of candidate shapes of the ring-shaped structure obtained from an exhaustive search of combinations of independently variable torsion angles of the ring-shaped structure, a system comprising:

a memory element for storing the set of candidate shapes of the ring-shaped structure, obtained from the exhaustive search, and logic signals; and a central processing unit including means for accessing the memory element and for using the logic signals such that the central processing unit defines means for generating coordinates for atoms in a candidate chain of the ring-shaped structure for each candidate shape in the set of candidate shapes.

8. In a computer system for estimating at least one shape of a molecule including a chain of a ring-shaped structure, from a set of candidate shapes of the ring-shaped structure obtained from an exhaustive search of combinations of independently variable parameters of the ring-shaped structure, a system comprising:

means for receiving the set of candidate shapes of the ring-shaped structure obtained from the exhaustive search; and means for generating coordinates of atoms in a candidate chain of the ring-shaped structure for each candidate shape in the set of candidate shapes.

9. The system of claim 8, further comprising means for screening each candidate chain against experimental data which indicate predetermined characteristics of the molecule.

10. A computer-readable database of at least one candidate shape of a ring-shaped molecule developed by a process of estimating a shape of the ring-shaped molecule from bond angles and bond lengths of the ring-shaped molecule, the process comprising the steps of:

identifying a candidate combination of values for independently variable parameters of the ring-shaped molecule;

selecting first and second adjacent atoms of the the ring, wherein the first and second atoms define a broken bond;

for the indentified candiate combination, determining coordinates of atoms of the ring-shaped molecule in a sequence from the first atom to the second atom according to the bond angles, the identified candidate combination of values and the bond lengths;

comparing a distance between the determined coordinates of the first and second atoms of the ring to an acceptable range of a bond length of the broken bond between the first and second atoms to determine whether the determined coordinates define a physically possible ring; and storing in the database an indication of the identified candidate combination as a candidate shape if the determined coordinates define a physically possible ring.

11. A computer system comprising a computer-readable medium, means for accessing information stored on the computer-readable medium, and an indication of a candidate shape of a ring of atoms stored on the medium and developed by a computer-implemented process using an indication of atoms of the flag, bond angles and bond lengths of the ring-shaped structure, the computer-implemented process comprising the steps of:

identifying a candidate combination of values for independently variable parameters of the ring of atoms;

selecting first and second adjacent atoms of the ring, wherein the first and second atoms define a broken bond;

determining, for the identified candidate combination, coordinates of atoms of the ring in a sequence from the first and second atom according to the bond angles, the identified candidate combination of values and the bond lengths;

comparing a distance between the determined coordinates of the first and second atoms of the ring to an acceptable range of a bond length of the broken bond between the first and second atoms to determine whether the determined coordinates define a physically possible ring; and storing on the computer-readable medium, in a manner to allow access using the indication of the candidate shape of the ring, an indication of the candidate combination as a candidate shape if the determined coordinates define a physically possible ring.

12. A computer-implemented process for using a computer-readable database of candidate shapes of a ring-shaped molecule prepared through an exhaustive search of combinations of independently variable parameters of the ring-shaped molecule, for estimating a plurality of candidate shapes of a molecule comprising the ring-shaped molecule, the process comprising the steps of:

accessing the computer-readable database to retrieve one of the candidate shapes of the ring-shaped molecule;

generating, using a computer and the retrieved candidate shapes, an estimate of the shape of the molecule comprising the ring-shaped molecule; and repeating the steps of accessing and generating for another of the candidate shapes of the ring-shaped molecule.

13. The process according to claim 1, wherein the selecting step includes using torsion angles of the ring, each torsion angle being selected according to a resolution and a range, the range being defined by an upper limit of the torsion angle and a lower limit of the torsion angle.

14. The process according to claim 13, wherein the selecting step includes:

defining a broken bond between two atoms of the ring, the broken bond having a known bond length and known bond angles thereabout;

setting variables to define the lower limit and the upper limit of the range for each torsion angle;

obtaining the bond lengths, the bond angles and a tolerance for each of the bond lengths and the bond angles of the ring; and for each torsion angle, incrementing the torsion angle independently of other torsion angles from the lower limit of the torsion angle to the upper limit of the torsion angle according to the resolution of the torsion angle.

15. The process according to claim 14, wherein the determining step includes calculating, for each atom in the ring, a vector which corresponds to a position of the atom, the determining step further including:

storing the bond angles of the atoms in the ring in a first vector;

storing the torsion angles of the atoms in the ring in a second vector;

storing the bond lengths of the atoms in the ring in a matrix;

selecting an origin corresponding to a position of an atom of the ring; and using coordinate transformation relations to calculate, for each atom in the ring, the vector corresponding to the position of the atom so as to yield the candidate combination.

16. The process according to claim 15, further comprising testing the candidate combination by:

determining a calculated bond length between the atoms of the broken bond using, for each atom of the broken bond, the vector corresponding to the position of the atom;

determining calculated bond angles for the atoms about the broken bond using, for each atom about the broken bond, the vector corresponding to the position of the atom;

determining a bond length tolerance based on the known bond length between the atoms defining the broken bond and a resolution of the known bond length of the atoms defining the broken bond;

determining, for each bond angle about the broken bond, a bond angle tolerance based on a known angle for atoms about the broken bond and a resolution of the known bond angle of the atoms about the broken bond;

rejecting a candidate combination having a calculated bond length between the atoms of the broken bond outside the bond length tolerance; and for each bond angle about the broken bond, rejecting a candidate combination having a calculated bond angle for atoms about the broken bond outside the bond angle tolerance.

17. The process according to claim 15, further comprising a step of applying a statistical analysis to the indication.

18. The process according to claim 16, further comprising a step of applying a statistical analysis to the indication.

19. A computer system according to claim 2, wherein the independently variable parameters include torsion angles of the ring, each torsion angle having a resolution and a range, the range being defined by an upper limit of the torsion angle and a lower limit of the torsion angle.

20. A computer system according to claim 19, wherein the means for identifying includes:

means for defining a broken bond between two atoms of the ring, the broken bond having a known bond length and known bond angles thereabout;

means for setting variables to define the lower limit and the upper limit of the range for each torsion angle;

means for obtaining the bond lengths, the bond angles and a tolerance for each of the bond lengths and the bond angles of the rings; and means for incrementing, for each torsion angle, the torsion angle independently of other torsion angles from the lower limit of the torsion angle to the upper limit of the torsion angle according to the resolution of the torsion angle.

21. The computer system according to claim 20, wherein the determining means includes:

means for storing the bond angles of the atoms in the ring in a first vector;

means for storing the torsion angles of the atoms in the ring in a second vector;

means for storing the bond lengths of the atoms in the ring in a matrix;

means for selecting an origin corresponding to a position of an atom of the ring; and means for using coordinate transformation relations to calculate, for each atom in the ring, a vector corresponding to the position of the atom so as to yield the candidate combination.

22. The computer system according to claim 21, wherein the determining means further includes:

means for determining a calculated bond length between the atoms of the broken bond using, for each atom of the broken bond, the vector corresponding to the position of the atom;

means for determining calculated bond angles for the atoms about the broken bond using, for each atom about the broken bond, the vector corresponding to the position of the atom;

means for determining a bond length tolerance based on the known bond length between the atoms defining the broken bond and a resolution of the known bond length of the atoms defining the broken bond;

means for determining, for each bond angle about the broken bond, a bond angle tolerance based on a known angle for atoms about the broken bond and a resolution of the known bond angle of the atoms about the broken bond;

means for rejecting a candidate combination having a calculated bond length between the atoms of the broken bond outside the bond length tolerance; and means for rejecting, for each bond angle about the broken bond, a candidate combination having a calculated bond angle for atoms about the broken bond outside the bond angle tolerance.

23. The computer system according to claim 21, further comprising means for applying a statistical analysis to the indication.

24. The computer systems according to claim 22, further comprising means for applying a statistical analysis to the indication.

25. A computer system according to claim 3, wherein the independently variable parameters include torsion angles of the ring, each torsion angle being selected according to a resolution and a range, the range being defined by an upper limit of the torsion angle and a lower limit of the torsion angle.

26. A computer system according to claim 25, wherein the means for identifying includes:

means for defining a broken bond between two atoms of the ring, the broken bond having a known bond length and known bond angles thereabout;

means for setting variables to define the lower limit and the upper limit of range for each torsion angle;

means for obtaining the bond lengths, the bond angles and the tolerance for each of the bond lengths and the bond angles of the ring; and means for incrementing, for each torsion angle, the torsion angle independently of other torsion angles from the lower limit of the torsion angle to the upper limit of the torsion angle according to the resolution of the torsion angle.

27. The computer system according to claim 26, wherein the determining means includes:

means for storing the bond angles of the atoms in the ring in a first vector;

means for storing the torsion angles of the atoms in the ring in a second vector;

means for storing the bond lengths of the atoms in the ring in a matrix;

means for selecting an origin corresponding to a position of an atom of the ring; and means for using coordinate transformation relations to calculate, for each atom in the ring, a vector corresponding to the position of the atom so as to yield the candidate combination.

28. The computer system according to claim 27, wherein the determining means further includes:

means for determining a calculated bond length between the atoms of the broken bond using, for each atom of the broken bond, the vector corresponding to the position of the atom;

means for determining calculated bond angles for the atoms about the broken bond using, for each atom about the broken bond, the vector corresponding to the position of the atom;

means for determining a bond length tolerance based on the known bond length between the atoms defining the broken bond and a resolution of the known bond length of the atoms defining the broken bond;

means for determining, for each bond angle about the broken bond, a bond angle tolerance based on a known angle for atoms about the broken bond and a resolution of the known bond angle of the atoms about the broken bond;

means for rejecting a candidate combination having a calculated bond length between the atoms of the broken bond outside the bond length tolerance; and means for rejecting, for each bond angle about the broken bond, a candidate combination having a calculated bond angle for atoms about the broken bond outside the bond angle tolerance.

29. The computer system according to claim 28, further comprising means for applying a statistical analysis to the indication.

30. The computer systems according to claim 29, further comprising means for applying a statistical analysis to the indication.

31. A computer system according to claim 4, wherein the independently variable parameters include torsion angles of the ring, each torsion angle being selected according to a resolution and a range, the range being defined by an upper limit of the torsion angle and a lower limit of the torsion angle.

32. The computer system according to claim 31, wherein the ring analysis module includes:

means for defining a broken bond between two atoms of the ring, the broken bond having a known bond length and known bond angles thereabout;

means for setting variables to define the lower limit and the upper limit of the range for each torsion angle;

means for obtaining the bond lengths, the bond angles and a tolerance for each of the bond lengths and the bond angles of the rings; and means for each torsion angle, incrementing the torsion angle independently of other torsion angles from the lower limit of the torsion angle to the upper limit of the torsion angle according to the resolution of the torsion angle.

33. The computer system according to claim 32, wherein the ring analysis module includes means for determining the coordinates of the atoms defining the ring by calculating, for each item in the ring, a vector which corresponds to a position of the atom, the determining means including:

means for storing the bond angles of the atoms in the ring in a first vector;

means for storing the torsion angles of the atoms in the ring in a second vector;

means for storing the bond lengths of the atoms in the ring in a matrix;

means for selecting an origin corresponding to a position of an atom of the ring; and means for using coordinate transformation relations to calculate, for each atom in the ring, the vector corresponding to the position of the atom so as to yield the candidate combination.

34. The computer system according to claim 33, wherein the ring analysis module includes:

means for determining a calculated bond length between the atoms of the broken bond using, for each atom of the broken bond, the vector corresponding to the position of the atom;

means for determining calculated bond angles for the atoms about the broken bond using, for each atom about the broken bond, the vector corresponding to the position of the atom;

means for determining a bond length tolerance based on the known bond length between the atoms defining the broken bond and a resolution of the known bond length of the atoms defining the broken bonds;

means for determining, for each bond angle about the broken bond, a bond angle tolerance based on a known angle for atoms about the broken bond and a resolution of the known bond angle of the atoms about the broken bond;

means for rejecting a candidate combination having a calculated bond length between the atoms of the broken bond outside the bond length tolerance; and means for rejecting, for each bond angle about the broken bond, a candidate combination having a calculated bond angle for atoms about the broken bond outside the bond angle tolerance.

35. The computer system according to claim 4, wherein the repetitive structure analysis module includes:

means for connecting candidate shapes through a multivalent atom so as to form torsion angles about the multivalent atom;

means for varying each torsion angle about the multivalent atom independently about the multivalent atom between a lower limit and an upper limit according to a resolution;

means for determining the coordinates of the atoms of the chain of rings;

means for rejecting a candidate shape having at least one bond length outside a physically acceptable range of the at least one bond length; and means for rejecting a candidate shape having at least one bond angle outside a physically acceptable range of the at least one bond angle.

36. The computer system according to claim 34, wherein the repetitive structure analysis module includes:

means for connecting candidate shapes through a multivalent atom so as to form torsion angles about the multivalent atom;

means for varying each torsion angle independently about the multivalent atom between a lower limit and an upper limit according to a resolution;

means for determining the coordinates of the atoms of the chain of rings;

means for rejecting a candidate shape having at least one bond length outside a physically acceptable range of the at least one bond length; and means for rejecting a candidate shape having at least one bond angle outside a physically acceptable range of the at least one bond angle.

37. A computer system according to claim 5, wherein the independently variable parameters include torsion angles of the ring, each torsion angle being selected according to a resolution and a range, the range being defined by an upper limit of the torsion angle and a lower limit of the torsion angle.

38. The computer system according to claim 37, wherein the first module includes:

means for defining a broken bond between two atoms of the ring, the broken bond having a known bond length and known bond angles thereabout;

means for setting variables to define the lower limit and the upper limit of the range for each torsion angle;

means for obtaining the bond lengths, the bond angles and a tolerance for each of the bond lengths and the bond angles of the rings; and means for each torsion angle, incrementing the torsion angle independently of other torsion angles from the lower limit of the torsion angle to the upper limit of the torsion angle according to the resolution of the torsion angle.

39. The computer system according to claim 38, wherein the first module further includes means for providing as the output the coordinates of the atoms defining the ring by calculating, for each item in the ring, a vector which corresponds to a position of the atom, the providing means including:

means for storing the bond angles of the atoms in the ring in a first vector;

means for storing the torsion angles of the atoms in the ring in a second vector;

means for storing the bond lengths of the atoms in the ring in a matrix;

means for selecting an origin corresponding to a position of an atom of the ring; and means for using coordinate transformation relations to calculate, for each atom in the ring, the vector corresponding to the position of the atom so as to yield the candidate combination.

40. The computer system according to claim 5, wherein the second module includes means for providing the output indicative of the candidate combination of the parameters which define a possible physical ring, the means for providing including:

means for determining a calculated bond length between the atoms of the broken bond using, for each atom of the broken bond, the vector corresponding to the position of the atom;

means for determining calculated bond angles for the atoms about the broken bond using, for each atom about the broken bond, the vector corresponding to the position of the atom;

means for determining a bond length tolerance based on the known bond length between the atoms defining the broken bond and a resolution of the known bond length of the atoms defining the broken bonds;

means for determining, for each bond angle about the broken bond, a bond angle tolerance based on a known angle for atoms about the broken bond and a resolution of the known bond angle of the atoms about the broken bond;

means for rejecting a candidate combination having a calculated bond length between the atoms of the broken bond outside the bond length tolerance; and means for rejecting, for each bond angle about the broken bond, a candidate combination having a calculated bond angle for atoms about the broken bond outside the bond angle tolerance.

41. The computer system according to claim 39, wherein the second module includes means for providing the output indicative of the candidate combination of the parameters which define a possible physical ring, the means for providing including:

means for determining a calculated bond length between the atoms of the broken bond using, for each atom of the broken bond, the vector corresponding to the position of the atom;

means for determining calculated bond angles for the atoms about the broken bond using, for each atom about the broken bond, the vector corresponding to the position of the atom;

means for determining a bond length tolerance based on the known bond length between the atoms defining the broken bond and a resolution of the known bond length of the atoms defining the broken bonds;

means for determining, for each bond angle about the broken bond, a bond angle tolerance based on a known angle for atoms about the broken bond and a resolution of the known bond angle of the atoms about the broken bond;

means for rejecting a candidate combination having a calculated bond length between the atoms of the broken bond outside the bond length tolerance; and means for rejecting, for each bond angle about the broken bond, a candidate combination having a calculated bond angle for atoms about the broken bond outside the bond angle tolerance.

42. The process according to claim 6, wherein the generating step includes:

individually varying each torsion angle formed about a muitivalent atom which links candidate shapes to yield the candidate chain, wherein each torsion angle formed about the muitivalent atom is varied from a first lower limit to a first upper limit according to a first resolution.

43. The process according to claim 42, wherein the generating step further includes:

eliminating a portion of a first range for each torsion angle; and varying each torsion angle over a second range, the second range being smaller than the first range, according to a second resolution, the second resolution being smaller than the first resolution.

44. The process according to claim 43, wherein the generating step further includes:

producing a distance matrix which indicates a distance from each atom to each atom in the candidate chain.

45. The process according to claim 44, wherein the generating step further includes:

rejecting a candidate chain having a distance from a first atom to a second atom which is not within a physically acceptable range for the distance between the first atom and the second atom.

46. A computer system according to claim 7, wherein the independently variable parameters include torsion angles of the ring, each torsion angle being selected according to a resolution and a range, the range being defined by an upper limit of the torsion angle and a lower limit of the torsion angle.

47. The system according to claim 46, wherein the means for generating coordinates includes:

means for eliminating a portion of a first range for each torsion angle; and means for varying each torsion angle over a second range, the second range being smaller than that first range, according to a second resolution, the second resolution being smaller than the first resolution.

48. The system according to claim 47, wherein the means for generating coordinates further includes means for producing a distance matrix which indicates a distance from each atom to each atom in the candidate chain.

49. The system according to claim 48, wherein the means for generating coordinates further includes means for rejecting a candidate chain having a distance from a first atom to a second atom which is not within a physically acceptable range for the distance between the first atom and the second atom.

50. The system according to claim 8, wherein the means for generating coordinates includes:

means for individually varying each torsion angle formed about a multivalent atom which links candidate shapes to yield a candidate chain, wherein each torsion angle formed about the multivalent atom is varied from a first lower limit to a first upper limit according to a first resolution.

51. The system according to claim 50, wherein the means for generating coordinates includes:

means for eliminating a portion of a first range for each torsion angle; and means for varying each torsion angle over a second range, the second range being smaller than that first range, according to a second resolution, the second resolution being smaller than the first resolution.

52. The system according to claim 51, wherein the means for generating coordinates includes means for producing a distance matrix which indicates a distance from each atom to each atom in the candidate chain.

53. The system according to claim 52, wherein the means for generating coordinates includes means for rejecting a candidate chain having a distance from a first atom to a second atom which is not within a physically acceptable range for the distance between the first atom and the second atom.

54. The system according to claim 9, wherein the means for generating coordinates includes:

means for individually varying each torsion angle formed about a multivalent atom which links candidate shapes to yield a candidate chain, wherein each torsion angle formed about the multivalent atom is varied from a first lower limit to a first upper limit according to a first resolution.

55. The system according to claim 54, wherein the means for generating coordinates includes:

means for eliminating a portion of a first range for each torsion angle; and means for varying each torsion angle over a second range, the second range being smaller than that first range, according to a second resolution, the second resolution being smaller than the first resolution.

56. The system according to claim 55, wherein the means for generating coordinates includes means for producing a distance matrix which indicates a distance from each atom to each atom in the candidate chain.

57. The system according to claim 56, wherein the means for generating coordinates includes means for rejecting a candidate chain having a distance from a first atom to a second atom which is not within a physically acceptable range for the distance between the first atom and the second atom.

58. The process according to claim 10, wherein the identifying step includes using torsion angles of the ring, each torsion angle being selected according to a resolution and a range, the range being defined by an upper limit of the torsion angle and a lower limit of the torsion angle.

59. The process according to claim 58, wherein the identifying step includes:

defining a broken bond between two atoms of the ring, the broken bond having a known bond length and known bond angles thereabout;

setting variables to define the lower limit and the upper limit of the range for each torsion angle;

obtaining the bond lengths, the bond angles and a tolerance for each of the bond lengths and the bond angles of the ring; and for each torsion angle, incrementing the torsion angle independently of other torsion angles from the lower limit of the torsion angle to the upper limit of the torsion angle according to the resolution of the torsion angle.

60. The process according to claim 59, wherein the determining step includes using a ring analysis module to calculate, for each atom in the ring, a vector which corresponds to a position of the atom, the determining step further including:

storing the bond angles of the atoms in the ring in a first vector;

storing the torsion angles of the atoms in the ring in a second vector;

storing the bond lengths of the atoms in the ring in a matrix;

selecting an origin corresponding to a position of an atom of the ring; and using coordinate transformation relations to calculate, for each atom in the ring, the vector corresponding to the position of the atom so as to yield the candidate combination.

61. The process according to claim 60, further comprising testing the candidate combination determining a calculated bond length between the atoms of the broken bond using, for each atom of the broken bond, the vector corresponding to the position of the atom;

determining calculated bond angles for the atoms about the broken bond using, for each atom about the broken bond, the vector corresponding to the position of the atom;

determining a bond length tolerance based on the known bond length between the atoms defining the broken bond and a resolution of the known bond length of the atoms defining the broken bond;

determining, for each bond angle about the broken bond, a bond angle tolerance based on a known angle for atoms about the broken bond and a resolution of the known bond angle of the atoms about the broken bond;

rejecting a candidate combination having a calculated bond length between the atoms of the broken bond outside the bond length tolerance; and for each bond angle about the broken bond, rejecting a candidate combination having a calculated bond angle for atoms about the broken bond outside the bond angle tolerance.

62. The process according to claim 60, further comprising a step of applying a statistical analysis to the indication.

63. The process according to claim 61, further comprising a step of applying a statistical analysis to the indication.

64. The process according to claim 11, wherein the identifying step includes torsion angles of the ring, each torsion angle having a resolution and a range, the range being defined by an upper limit of the torsion angle and a lower limit of the torsion angle.

65. The process according to claim 64, wherein the identifying step includes:

defining a broken bond between two atoms of the ring, the broken bond having a known bond length and known bond angles thereabout;

setting variables to define the lower limit and the upper limit of the range for each torsion angle;

obtaining the bond lengths, the bond angles and a tolerance for each of the bond lengths and the bond angles of the rings; and for each torsion angle, incrementing the torsion angle independently of other torsion angles from the lower limit of the torsion angle to the upper limit of the torsion angle according to the resolution of the torsion angle.

66. The process according to claim 65, wherein the determining means includes a ring analysis module capable of:

storing the bond angles of the atoms in the ring in a first vector;

storing the torsion angles of the atoms in the ring in a second vector;

storing the bond lengths of the atoms in the ring in a matrix;

selecting an origin corresponding to a position of an atom of the ring; and using coordinate transformation relations to calculate, for each atom in the ring, a vector corresponding to the position of the atom so as to yield the candidate combination.

67. The process according to claim 66, wherein the determining step includes:

determining a calculated bond length between the atoms of the broken bond using, for each atom of the broken bond, the vector corresponding to the position of the atom;

determining calculated bond angles for the atoms about the broken bond using, for each atom about the broken bond, the vector corresponding to the position of the atom;

determining a bond length tolerance based on the known bond length between the atoms defining the broken bond and a resolution of the known bond length of the atoms defining the broken bond;

determining, for each bond angle about the broken bond, a bond angle tolerance based on a known angle for atoms about the broken bond and a resolution of the known bond angle of the atoms about the broken bond;

rejecting a candidate combination having a calculated bond length between the atoms of the broken bond outside the bond length tolerance; and for each bond angle about the broken bond, rejecting a candidate combination having a calculated bond angle for atoms about the broken bond outside the bond angle tolerance.

68. The process according to claim 12, wherein the generating step includes retrieving, for each atom in the ring, a vector which corresponds to a position of the atom, the generating step further including:

retrieving the bond angles of the atoms in the ring from a first vector;

retrieving the torsion angles of the atoms in the ring from a second vector;

retrieving the bond lengths of the atoms in the ring from a matrix;

selecting an origin corresponding to a position of an atom of the ring; and using coordinate transformation relations to calculate, for each atom in the ring, the vector corresponding to the position of the atom so as to yield the candidate combination.

69. The process according to claim 68, further comprising testing the candidate combination by:

determining a calculated bond length between the atoms of the broken bond using, for each atom of the broken bond, the vector corresponding to the position of the atom;

determining calculated bond angles for the atoms about the broken bond using, for each atom about the broken bond, the vector corresponding to the position of the atom;

determining a bond length tolerance based on the known bond length between the atoms defining the broken bond and a resolution of the known bond length of the atoms defining the broken bond;

determining, for each bond angle about the broken bond, a bond angle tolerance based on a known angle for atoms about the broken bond and a resolution of the known bond angle of the atoms about the broken bond;

rejecting a candidate combination having a calculated bond length between the atoms of the broken bond outside the bond length tolerance; and for each bond angle about the broken bond, rejecting a candidate combination having a calculated bond angle for atoms about the broken bond outside the bond angle tolerance.

70. The process according to claim 12, wherein the generating step includes retrieving, for each atom in the ring, a vector which corresponds to a position of the atom, the generating step further including:

retrieving the bond angles of the atoms in the ring in a first vector;

retrieving the torsion angles of the atoms in the ring in a second vector;

storing the bond lengths of the atoms in the ring in a matrix;

selecting an origin corresponding to a position of an atom of the ring; and using coordinate transformation relations to calculate, for each atom in the ring, the vector corresponding to the position of the atom so as to yield the candidate combination.

71. The process according to claim 70, further comprising testing the candidate combination by:

determining a calculated bond length between the atoms of the broken bond using, for each atom of the broken bond, the vector corresponding to the position of the atom;

determining calculated bond angles for the atoms about the broken bond using, for each atom about the broken bond, the vector corresponding to the position of the atom;

determining a bond length tolerance based on the known bond length between the atoms defining the broken bond and a resolution of the known bond length of the atoms defining the broken bond;

determining, for each bond angle about the broken bond, a bond angle tolerance based on a known angle for atoms about the broken bond and a resolution of the known bond angle of the atoms about the broken bond;

rejecting a candidate combination having a calculated bond length between the atoms of the broken bond outside the bond length tolerance; and for each bond angle about the broken bond, rejecting a candidate combination having a calculated bond angle for atoms about the broken bond outside the bond angle tolerance.

72. In a computer-implemented process for estimating at least one shape of a molecule including a ring of atoms, from bond angles and bond lengths of the ring defined by the atoms of the ring, a process comprising the steps, performed by a computer, of:

selecting a candidate combination of values for independently variable parameters of the ring of atoms;

for the selected candidate combination, determining coordinates of the atoms of the ring according to the bond angles, the selected candidate combination of values, and the bond lengths;

determining whether the determined coordinates define a physically possible ring; and recording an indication of the candidate combination as a candidate shape if the determined coordinates define a physically possible ring.

73. A computer-readable database of candidate shapes of a ring-shaped molecule, developed by a process of estimating a shape of the ring-shaped molecule from bond angles and bond lengths of the ring-shaped molecule, comprising:

a computer-readable medium having computer-readable signals stored thereon and indicative of all candidate combinations of values for independently variable parameters of the ring-shaped molecule given a range and resolution of the independently variable parameters such that coordinates of atoms of the ring-shaped molecule, defined by the bond angles, the identified candidate combination of values and the bond lengths, define a physically possible ring; and means for accessing the candidate shapes using an indication of the ring-shaped molecule.

* * * * *